US006288247B1

US 6,288,247 B1
(12) United States Patent
Andemichael et al.

(10) Patent No.: US 6,288,247 B1
(45) Date of Patent: Sep. 11, 2001

(54) PROCESS OF MAKING 3-PHENYL-1-METHYLENEDIOXYPHENYL-INDANE-2-CARBOXYLIC ACID DERIVATIVES

(75) Inventors: Yemane Woldeselassie Andemichael, Jeffersonville; Neil Howard Baine, Merion; William Morrow Clark, Philadelphia; Conrad John Kowalski, Paoli; Michael Anthony McGuire; Robert John Mills, both of Norristown, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/521,172

(22) Filed: Mar. 8, 2000

Related U.S. Application Data

(62) Division of application No. 09/068,581, filed as application No. PCT/US96/18846 on Nov. 8, 1996, now Pat. No. 6,147,232
(60) Provisional application No. 60/006,345, filed on Nov. 8, 1995.

(51) Int. Cl.[7] .................................................. C07D 317/44
(52) U.S. Cl. .............................................................. 549/447
(58) Field of Search ............................................. 549/447

(56) References Cited

U.S. PATENT DOCUMENTS

| 3,997,540 | 12/1976 | Mehta et al. . |
| 4,073,912 | 2/1978 | Kaiser et al. . |
| 5,389,620 | 2/1995 | Ishikawa et al. . |

FOREIGN PATENT DOCUMENTS

WO 93/08799    5/1993  (WO) .

OTHER PUBLICATIONS

Cardillo, et al.; Tetrahedron Letters, 1994, vol. 35, No. 28, pp. 5051–5054.

Primary Examiner—Deborah C. Lambkin
(74) Attorney, Agent, or Firm—Wayne J. Dustman; William T. King; Charles M. Kinzig

(57) ABSTRACT

Invented is an improved process for preparing aromatic ring-fused cyclopentane derivatives. Preferred compounds prepared by this invention are indane carboxylates and cyclopentano[b]pyridine derivatives. The most preferred compounds prepared by this invention are (+)(1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof and (+)(1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof. Also invented are novel intermediates useful in preparing these compounds.

33 Claims, No Drawings

PROCESS OF MAKING 3-PHENYL-1-METHYLENEDIOXYPHENYL-INDANE-2-CARBOXYLIC ACID DERIVATIVES

This is a divisional of application Ser. No. 09/068,581 filed May 8, 1998, now U.S. Pat. No. 6,147,232 which is a 371 of PCT/US96/18846, filed Nov. 8, 1996 and claims benefit of No. 60/006,345 Nov. 8, 1995.

FIELD OF THE INVENTION

The present invention relates to an improved process for preparing aromatic ring-fused cyclopentane derivatives. Preferably, the present invention relates to an improved process for preparing indane carboxylates and cyclopentano[b]pyridine derivatives. Advantageously, the present invention relates to an improved process for preparing (+) (1S, 2R, 3S)-3-[2-(2-hydroxyeth-1-yloxy)-4-methoxyphenyl[-1-(3, 4-methylenedioxyphenyl)-5-(prop-1-yloxy)indane-2-carboxylic acid and pharmaceutically acceptable salts thereof and (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof. Such compounds are described in International Application Number: PCT/US94/04603—International Publication Number WO 94/25013 published on Nov. 10, 1994 and in U.S. Pat. No. 5,389,620, as being useful as endothelin receptor antagonists. Also invented are novel intermediates useful in preparing these compounds.

BACKGROUND OF THE INVENTION

Processes for the preparation of indane carboxylates, specifically (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and (+) (1S, 2R, 3S)-3-(2-carboxymethoxy-4-methoxyphenyl)-1-(3,4-methylenedioxyphenyl)-5-(prop-1-yloxy)indane-2-carboxylic acid have previously been described. In particular a multistep process to prepare (+) (1S, 2R, 3S)-3-(2-carboxymethoxy-4-methoxyphenyl)-1-(3,4-methylenedioxyphenyl)-5-(prop-1-yloxy)indane-2-carboxylic acid in 6% overall yield (not including a racemic separation step) from methyl 3-(prop-1-yloxy) benzoylacetate and a multistep process to prepare (+) (1S, 2R, 3S)-3-[2-(2-hydroxyeth-1-yloxy)-4-methoxyphenyl[-1-(3,4-methylenedioxyphenyl)-5-(prop-1-yloxy)indane-2-carboxylic acid in 2% overall yield (not including a racemic separation step) from methyl 3-(prop-1-yloxy) benzoylacetate is reported in International Publication Number WO 94/25013, published Nov. 10, 1994. The syntheses of these molecules are complicated by the presence of three chiral centers in each compound.

Processes for the preparation of cyclopentano[b]pyridine derivatives have previously been described. In particular, multistep processes to prepare cyclopentano[b]pyridine derivatives, in low over all yield, are reported in U.S. Pat. No. 5,389,620.

Thus, there is a need in the art for an economical method to prepare indane carboxylates and cyclopentano[b]pyridine derivatives, specifically (+) (1S, 2R, 3S)-3-[2-(2-hydroxyeth-1-yloxy)4-methoxyphenyl]-1-(3,4-methylenedioxyphenyl)-5-(prop-1-yloxy)indane-2carboxylic acid and pharmaceutically acceptable salts thereof and (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof.

The numerous advantages of the presently invented process and intermediates will become apparent upon review of the following description.

SUMMARY OF THE INVENTION

This invention relates to an improved process for preparing aromatic ring-fused cyclopentane derivatives.

This invention also relates to novel intermediates useful in preparing aromatic ring-fused cyclopentane derivatives.

This invention relates to an improved process for preparing indane carboxylates.

This invention also relates to novel intermediates useful in preparing indane carboxylates.

This invention relates to an improved process for preparing cyclopentano[b]pyridine derivatives.

This invention also relates to novel intermediates useful in preparing cyclopentano[b]pyridine derivatives.

This invention relates to an improved process for preparing (+) (1S, 2R, 3S)-3-[2-(2-hydroxyeth-1-yloxy)-4methoxyphenyl]-1-(3,4-methylenedioxyphenyl)-5-(prop-1-yloxy)indane-2-carboxylic acid and pharmaceutically acceptable salts thereof, preferably the ethylene diamine 2:1 salt.

This invention relates to novel intermediates useful in preparing (+) (1S, 2R, 3S)-3-[2-(2-hydroxyeth-1-yloxy)4-methoxyphenyl]-1-(3,4-methylenedioxyphenyl)-5-(prop-1-yloxy)indane-2-carboxylic acid.

This invention relates to an improved process for preparing (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof, preferably the disodium salt.

This invention relates to novel intermediates useful in preparing (+) (1S, 2R, 3S)-3-(2-carboxymethoxy-4-methoxyphenyl)-1-(3,4-methylenedioxyphenyl)-5-(prop-1-yloxy)indane-2-carboxylic acid.

DETAILED DESCRIPTION OF THE INVENTION

Unless otherwise defined, the term 'aromatic ring-fused cyclopentane derivatives' as used herein, is meant the racemic compounds of Formula (1):

(1)

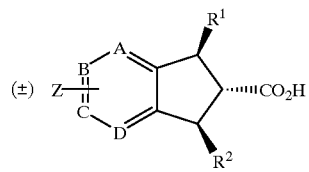

wherein A, B, C and D are carbon atoms or three of A, B, C and D are carbon atoms and one is a nitrogen atom;
$R^1$ is

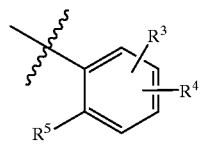

where $R^3$ and $R^4$ are independently H, OH, $C_{1-8}$alkoxy, F, $CF_3$ or $C_{1-6}$alkyl and $R^5$ is $-OCH_2CO_2H$ or $-OCH_2CH_2OH$;

$R^2$ is

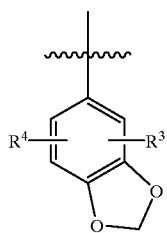

where $R^3$ and $R^4$ are as indicated above and

Z is H, OH, or $C_{1-5}$alkoxy;

or a pharmaceutically acceptable salt thereof.

Preferred among the racemic compounds of Formula (1) are the compounds of Formula (17):

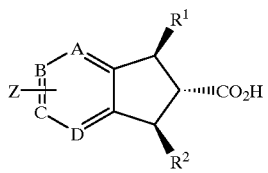

(17)

wherein A, B, C, D, $R^1$, $R^2$ and Z are as described in Formula (1);

or a pharmaceutically acceptable salt thereof.

By the term indane carboxylates as used herein is meant the racemic compounds of Formula (2):

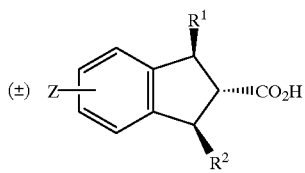

(2)

wherein $R^1$, $R^2$ and Z are as described in Formula (1);

or a pharmaceutically acceptable salt thereof.

Preferred among the racemic compounds of Formula (2) are the compounds of Formula (18):

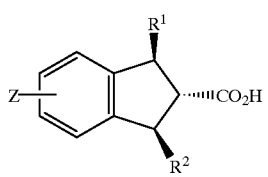

(18)

wherein $R^1$, $R^2$ and Z are as described in Formula (1);

or a pharmaceutically acceptable salt thereof.

By the term cyclopentano[b]pyridine derivatives as used herein is meant the racemic compounds of Formula (3):

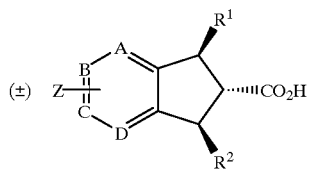

(3)

wherein three of A, B, C and D are carbon atoms and one is a nitrogen atom; and $R^1$, $R^2$ and Z are as described in Formula (1);

or a pharmaceutically acceptable salt thereof.

Preferred among the racemic compounds of Formula (3) are the compounds of Formula (19):

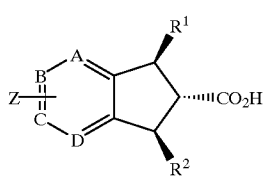

(19)

wherein three of A, B, C and D are carbon atoms and one is a nitrogen atom: and $R^1$, $R^2$ and Z are as described in Formula (1);

or a pharmaceutically acceptable salt thereof.

In Formula (3) compounds, in Formula (19) compounds and in Formula (1) compounds when one of A, B, C or D is a nitrogen atom, preferably A is nitrogen.

Pharmaceutically acceptable salts of the compounds of Formulas (1), (2), (3), (17), (18) and (19) are formed where appropriate by methods well known to those of skill in the art.

Pharmaceutically acceptable salts of (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and (+) (1S, 2R, 3S)-3-(2-carboxymethoxy-4-methoxyphenyl)-1-(3,4-methylenedioxyphenyl)-5-(prop-1-yloxy)indane-2-carboxylic acid are formed where appropriate by methods well known to those of skill in the art.

By the term "Pr" as used herein is meant n-propyl.

By the term "Ph" as used herein is meant phenyl.

As used in the specification and in the claims, unless otherwise defined, the term $X_c$ means a chiral auxiliary. By the term "chiral auxiliary" as used herein is meant a non-raceric functional group that imparts a diastereoselective reaction at a remote prochiral center of a molecule. Chiral auxiliaries as used herein are formed by reaction with a compound of the formula $HX_c$ wherein $X_c$ is as described above. Examples of $HX_c$ as used herein include: 8-phenylmenthol (such as described in D. Comins et al. *J. Org. Chem.*, vol. 58, 4656 (1993)), N-substituted borane-2,10-sultams (such as described in W. Oppolzer *J. Am. Chem. Soc.*, 112 2767 (1990)), preferably, 4-substituted or 4,5-substituted 2-oxazolidinones derived from amino acid derivatives such as phenylglycinol or valinol (such as described in D. Evans et al. *J. Am. Chem. Soc.*, 109, 6881 (1987) and in D. Evans et al. *Tet. Lett.*, 28, 1123 (1990)) and, most preferably, 4-substituted or 4,5-substituted 2-imidazolidinones derived from compounds such as ephedrine (such as described in S. E. Drewes, et al. *Chem. Ber.*, 126, 2663 (1993)). The most preferred "$X_c$" for use herein is the predominately optically pure substituent of the formula

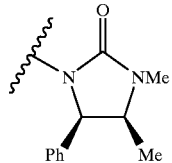

(ac)

Thus, the most preferred form of a chiral auxiliary for use herein is a compound of formula (u):

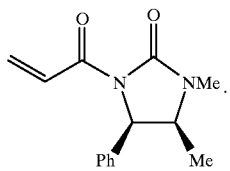

(u)

Additionally, the racemic compounds of Formulas (1), (2) and (3) are prepared as described herein by substituting the chiral $X_c$ substituent, as used herein, with an achiral group, such as an alkoxy or amine group.

The term 'activation reaction' for use herein refers to the numerous reactions and reaction conditions known to those skilled in the art to effect the introduction of a Br, I, —$OSO_2CF_3$ or a —$OSO_2F$ substituent.

The term (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid as used herein utilizes standard chemical terminology and refers to Compound (r)

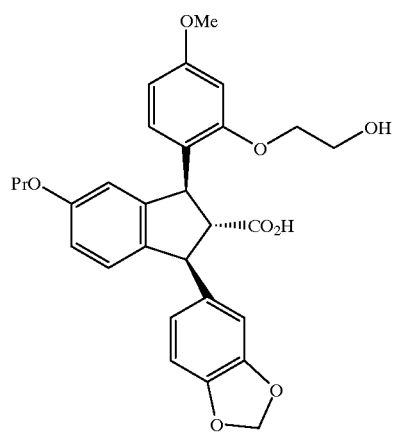

(r)

The term (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid ethylene diamine salt (2:1) as used herein utilizes standard chemical terminology and refers to Compound (s)

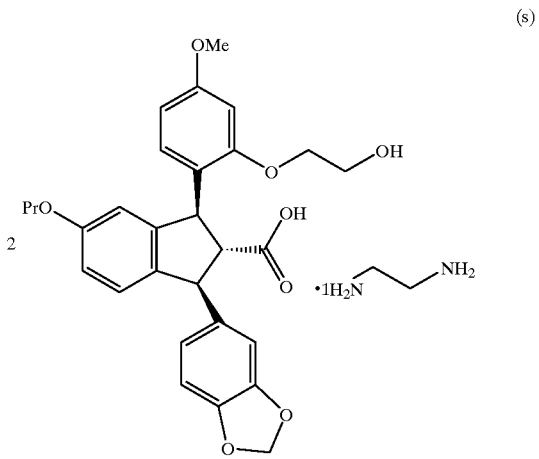

(s)

The term (+) (1S, 2R, 3S)-3-(2-carboxymethoxy-4-methoxyphenyl)-1-(3,4-methylenedioxyphenyl)-5-(prop-1-yloxy)indane-2-carboxylic acid as used herein utilizes standard chemical terminology and refers to Compound (j)

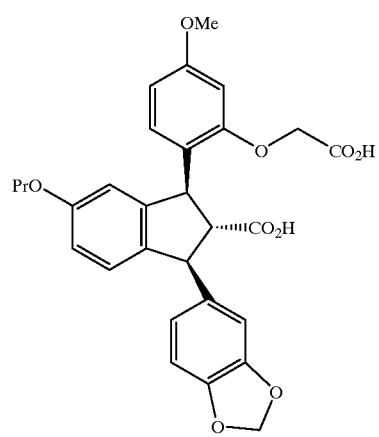

(j)

The term (+) (1S, 2R, 3S)-3-(2-carboxymethoxy-4-methoxyphenyl)-1-(3,4-methylenedioxyphenyl)-5-(prop-1-yloxy)indane-2-carboxylic acid disodium salt as used herein utilizes standard chemical terminology and refers to Compound (k)

(k)

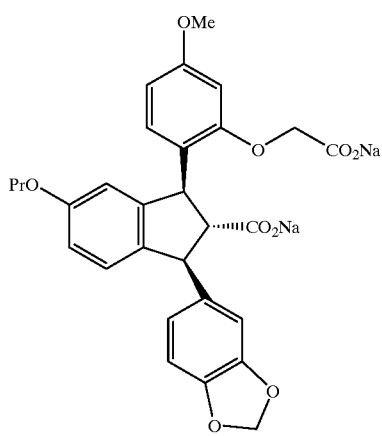

The indane carboxylates of Formula (18) of the current invention are prepared by methods outlined in the Schemes below and in the Examples from compounds of Formula (a).

(a)

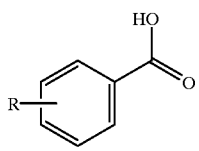

where R is H, OH, $C_{1-5}$alkoxy (preferably n—PrO) or a protected oxy group, such as benzyloxy. Compounds of Formula (a) are known or can be prepared from readily available starting materials by those skilled in the art.

By the term 'protected oxy group' and 'protected OH' as used herein, is meant any conventional blocking group in the art such as described in "Protective Groups in Organic Synthesis" by Theodora W. Greene. Wiley-Interscience, 1981, New York, provided that such protected oxy groups or such protected OH do not include moieties that render inoperative the presently invented process. A preferred protected oxy group for use herein is benzyloxy. A preferred protected OH for use herein is benzyloxy.

Further, when necessary or desired, R can be converted to a substituent of Z. Reactions to convert R to Z are performed on products of the synthetic pathways disclosed or claimed herein or, where appropriate or preferable on certain intermediates in these synthetic pathways. For example, hydroxyl groups can be converted into $C_{1-5}$alkoxy groups by alkylation. Protected oxy groups can be deprotected and further reacted to form a substituent of Z.

The present invention provides an improved process for the production of indane carboxylates of Formula (18) as indicated in Schemes 1 and 2 below.

Scheme 1

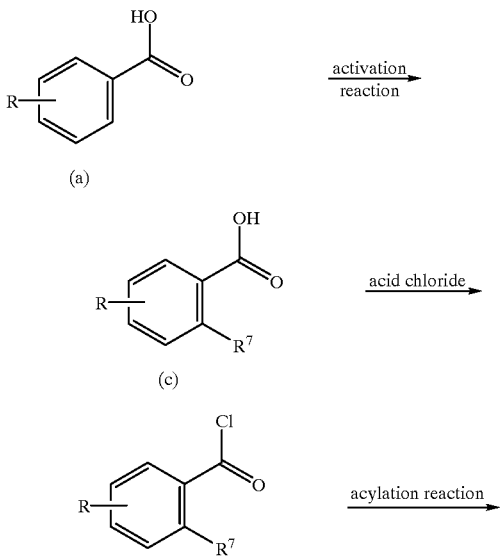

-continued
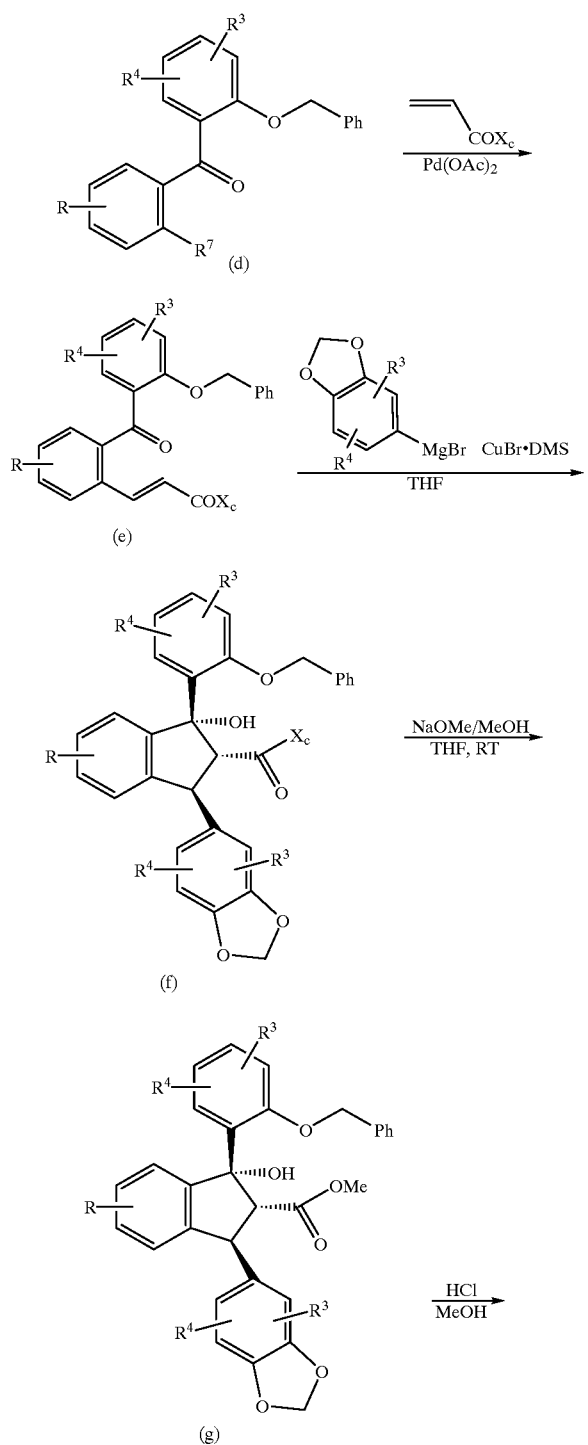

-continued
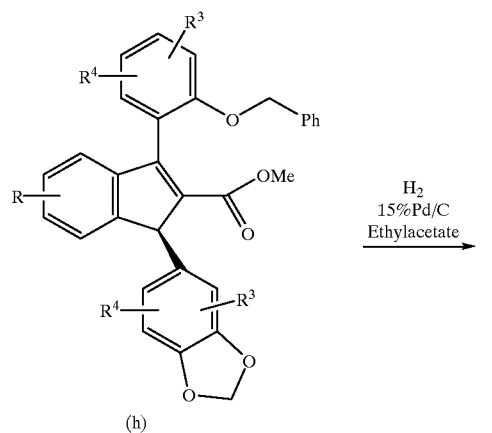
(h)
H₂
15%Pd/C
Ethylacetate
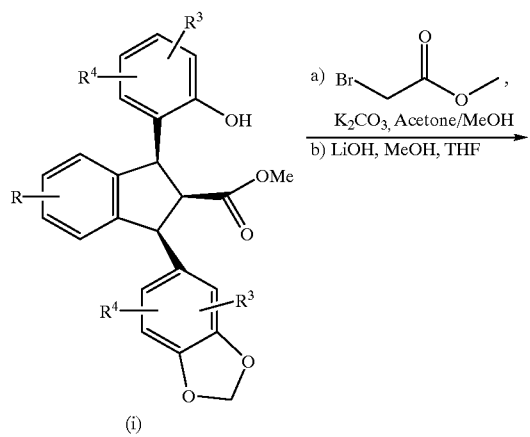
(i)
a) Br⌐⌐CO₂Me,
K₂CO₃, Acetone/MeOH
b) LiOH, MeOH, THF
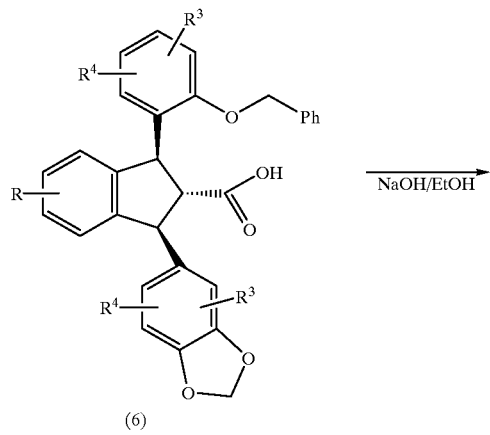
(6)
NaOH/EtOH

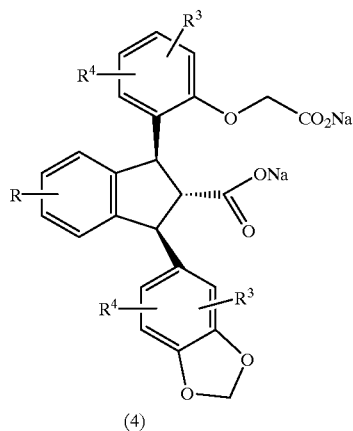

(4)

Scheme 1 outlines formation of indane carboxylates wherein $R^5$ is —$OCH_2CO_2H$, preferably the disodium salt, Compound (k). As used in Scheme 1, $R^3$ and $R^4$ are as described in Formula (1), R is as described in Formula (a) and $R^7$ is Br, I, —$OSO_2CF_3$ or —$OSO_2F$. Compounds of Formula (c) are prepared in one or more steps by treating a compound of Formula (a) in an activation reaction, preferably with bromine in methylene chloride, to introduce substituent $R^7$. Compounds of Formula (d) are prepared by reacting a compound of Formula (c) with an acid chloride, such as thionyl chloride, and using this product as an acylating agent in a reaction, such as a Grignard reaction with a compound of Formula (t) as defined on page 32, or a Friedel-Crafts reaction, such as described in Example 1, step (iii). Compounds of Formula (e) are prepared by reacting a compound of Formula (d) with a chiral auxiliary in the presence of palladium(II) acetate/triphenylphosphine catalyst. Treatment of a compound of Formula (e) with an appropriately substituted 3,4-(methylenedioxy) phenylmagnesium bromide (which can be readily prepared from commercially available starting materials) and a copper complex, such as copper(I) bromide-dimethylsulfide complex (which is commercially available from the Aldrich Chemical Co. of Milwaukee, Wis.), in tetrahydrofuran followed by crystallization gives compounds of Formula (f) as the predominately pure diastereomer. Treatment of a compound of Formula (f) with sodium methoxide/methanol gives compounds of Formula (g). Compounds of Formula (h) are prepared by treating a compound of Formula (g) in methanol with anhydrous acid. Compounds of Formula (i) are prepared by hydrogenating a compound of Formula (h) over palladium on carbon. Treating a compound of Formula (i) with methyl bromoacetate and potassium carbonate in acetone/methanol, followed by saponification/epimerization effected with lithium hydroxide monohydrate and acid workup yields the corresponding diacid of Formula (6) (preferably Compound (j) as used herein). Compounds of Formula (6) are treated with sodium hydroxide to give compounds of Formula (4) (preferably Compound (k) as used herein). Additionally, treating a compound of Formula (i) with ethylene carbonate/potassium carbonate in toluene at 90–115° C. followed by saponification/epimerization with lithium hydroxide and acidic work up is a preferred method for preparing a compound of Formula (7). It is readily apparent to those of skill in the art that the substituent —$OCH_2Ph$ in the above Scheme is functioning as a protected OH and that another protected OH group could be utilized in its place or that, under appropriate circumstances, the unprotected OH could be utilized.

Scheme 2

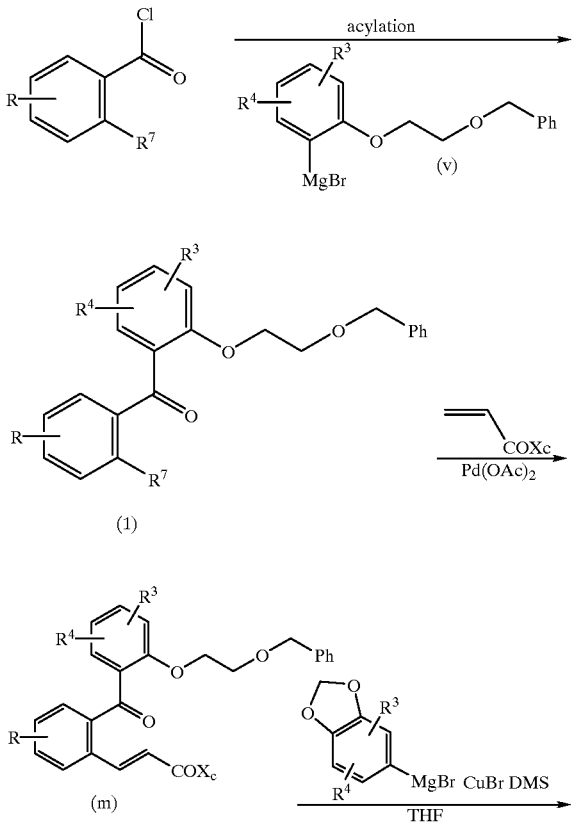

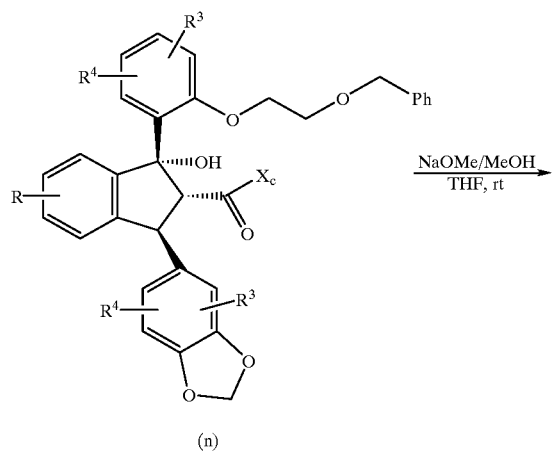
(n)
NaOMe/MeOH
THF, rt
→
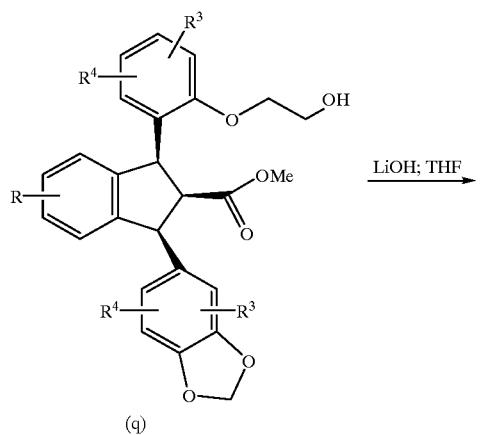
(q)
LiOH; THF
→
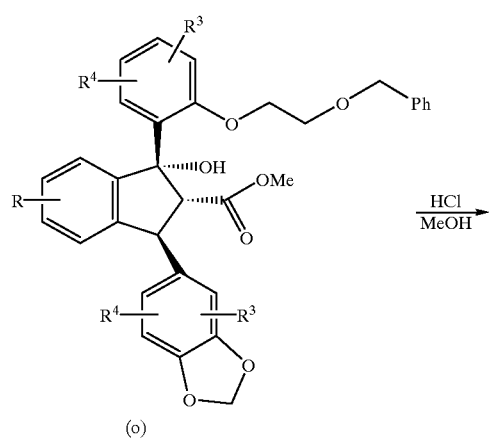
(o)
HCl
MeOH
→
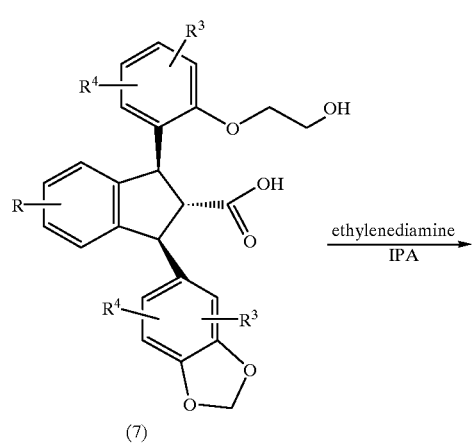
(7)
ethylenediamine
IPA
→
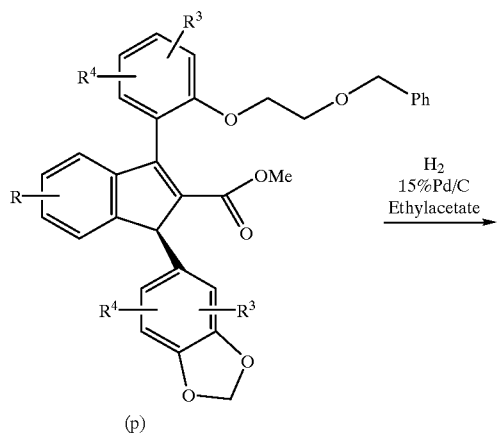
(p)
H₂
15%Pd/C
Ethylacetate
→
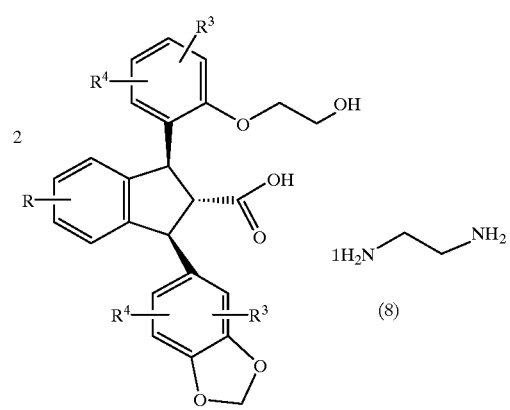
(8)

Scheme 2 outlines formation of indane carboxylates wherein $R^5$ is —$OCH_2CH_2OH$, preferably the ethylene diamine salt (2:1), Compound (s). As used in Scheme 2, $R^3$ and $R^4$ are as described in Formula (1), R is as described in Formula (a) and $R^7$ is Br, I, —$OSO_2CF_3$ or —$OSO_2F$. The acid chloride of the compounds of Formula (c) from Scheme 1 are reacted in an acylation reaction, preferably in a Grignard reaction with a compound of Formula (v) prepared as described on page 33, to give compounds of Formula (1). Compounds of Formula (m) are prepared by reacting a compound of Formula (1) with a chiral auxiliary in the presence of palladium(II) acetateltriphenylphosphine catalyst. Treatment of a compound of Formula (m) with an appropriately substituted 3,4-(methylenedioxy)phenylmagnesium bromide (which can be readily prepared from commercially available starting materials) and a copper complex, preferably a copper (I) salt such as CuCl, CuBr, CuCN or most preferably copper(I) bromide-dimethylsulfide complex (which is commercially available from the Aldrich Chemical Co. of Milwaukee, Wis.) in tetrahydrofuran gives compounds of Formula (n) as the predominately pure diastereomer. Treatment of a compound of Formula (n) with sodium methoxide/methanol gives compounds of Formula (o). Compounds of Formula (p) are prepared by treating a compound of Formula (o) in methanol with anhydrous acid. Compounds of Formula (q) are prepared by hydrogenating compounds of Formula (p) over palladium on carbon. Treatment of compounds of Formula (q) with lithium hydroxide monohydrate followed by acidic workup gives the acid of Formula (7) (preferably Compound (r) as used herein). Compounds of Formula (7) are treated with ethylene diamine to give compound of Formula (8) (preferably Compound (s) as used herein). It is readily apparent to those of skill in the art that the substituent —$OCH_2Ph$ in the above Scheme is functioning as a protected OH and that another protected OH group could be utilized in its place or that, under appropriate circumstances, the unprotected OH could be utilized.

The racemic compounds of Formulas (1), (2) and (3) are prepared according to the methods outlined in Schemes (1) and (2) and in the Examples by substituting a compound of Formula (9):

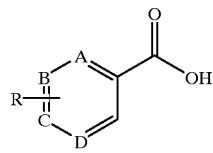

(9)

wherein A, B, C and D are carbon atoms or three of A, B, C and D are carbon atoms and one is a nitrogen atom and
R is H, OH, $C_{1-5}$alkoxy (preferably n-PrO) or a protected oxy group, such as benzyloxy,
for the compound of Formula (a) and by substituting the chiral $X_c$ substituent of the chiral auxiliary with an achiral group, such as an alkoxy or amnine group.

Compounds of Formula (9) are known or can be prepared from readily available starting materials by those skilled in the art.

Thus, an achiral group is substituted for the $X_c$ substituent of the chiral auxiliary in Schemes 1 and 2 to prepare compounds of Formula (2) and intermediates useful in preparing compounds of Formula (2). The compounds of Formula (9) are utilized in Schemes 1 and 2, by substituting the chiral $X_c$ substituent of the chiral auxiliary with an achiral group, to prepare compounds of Formula (1) and intermediates useful in preparing compounds of Formula (1). The compounds of Formula (9), wherein three of A, B, C and D are carbon atoms and one is a nitrogen atom, are utilized in Schemes 1 and 2, by substituting the chiral $X_c$ substituent of the chiral auxiliary with an achiral group, to prepare compounds of Formula (3) and intermediates useful in preparing compounds of formula (3).

The cyclopentano[b]pyridine derivatives of Formula (19) of the current invention are prepared according the methods outlined in Schemes 1 and 2 and in the Examples from compounds of Formula (9) wherein three of A, B, C and D are carbon atoms and one is a nitrogen atom. Preferred among Formula (9) compounds when a nitrogen is present are those wherein A is nitrogen.

The aromatic ring-fused cyclopentane derivatives of Formula (17) of the current invention are prepared according the methods outlined in Schemes 1 and 2 and in the Examples from compounds of Formula (9) wherein A, B, C and D are carbon atoms or three of A, B, C and D are carbon atoms and one is a nitrogen atom. Preferred among Formula (9) compounds when a nitrogen is present are those wherein A is nitrogen.

Prepared in synthesizing the indane carboxylates of Formula (18), preferably Compound (k) and Compound (s), are novel intermediates of Formula (c):

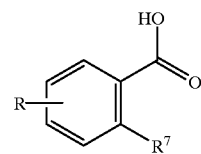

(c)

wherein R is as described in Formula (a) and $R^7$ is Br, I, —$OSO_2CF_3$ or —$OSO_2F$.

Also prepared in synthesizing the indane carboxylates of Formula (18), preferably Compound (k) and Compound (s), are novel intermediates of the formula:

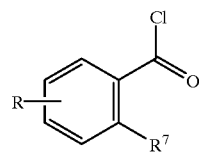

wherein R is as described in Formula (a) and $R^7$ is Br, I, —$OSO_2CF_3$ or —$OSO_2F$.

Also prepared in synthesizing the indane carboxylates of Formula (18), preferably Compound (k), are novel intermediates of Formula (d):

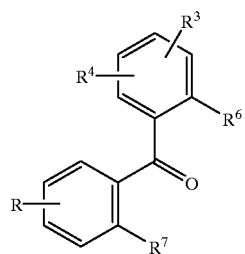
(d)

wherein $R^3$ and $R^4$ are as described in Formula (1), R is as described in Formula (a), $R^6$ is OH or a protected OH and $R^7$ is Br, I, —$OSO_2CF_3$ or —$OSO_2F$.

Also prepared in synthesizing the indane carboxylates of Formula (18), preferably Compound (k), are novel intermediates of Formula (e):

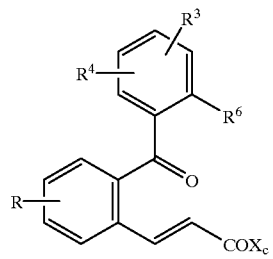
(e)

wherein $R^3$ and $R^4$ are as described in Formula (1), $X_c$ is as described above, R is as described in Formula (a) and $R^6$ is OH or a protected OH.

Also prepared in synthesizing the indane carboxylates of Formula (18), preferably Compound (k), are novel intermediates of Formula (f):

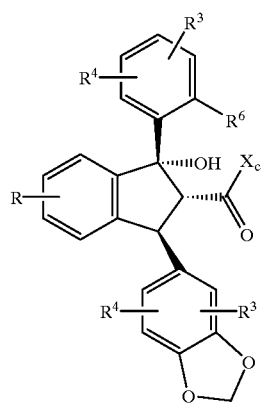
(f)

wherein $R^3$ and $R^4$ are as described in Formula (1), R is as described in Formula (a) and $R^6$ is OH or a protected OH.

Also prepared in synthesizing the indane carboxylates of Formula (18), preferably Compound (K), are novel intermediates of Formula (g):

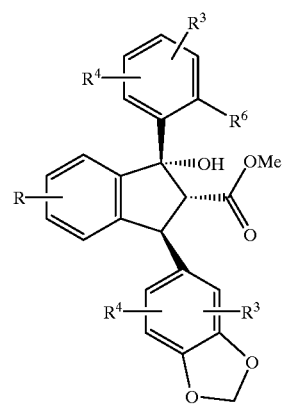
(g)

wherein $R^3$ and $R^4$ are as described in Formula (1), R is as described in Formula (a) and $R^6$ is OH or a protected OH.

Also prepared in synthesizing the indane carboxylates of Formula (18), preferably Compound (k), are novel intermediates of Formula (h):

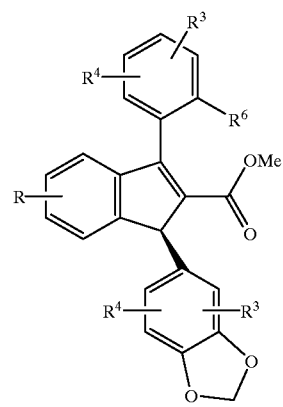
(h)

wherein $R^3$ and $R^4$ are as described in Formula (1), R is as described in Formula (a) and $R^6$ is OH or a protected OH.

Prepared in synthesizing the indane carboxylates of Formula (2), preferably Compound (k), are novel racemic intermediates of Formula (27):

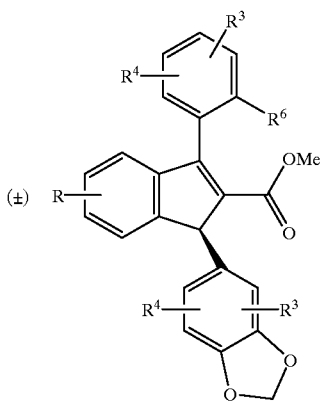
(27)

wherein $R^3$ and $R^4$ are as described in Formula (1), R is as described in Formula (a) and $R^6$ is OH or a protected OH.

Also prepared in synthesizing the indane carboxylates of Formula (18), preferably Compound (k) and Compound (s), are novel intermediates of Formula (i):

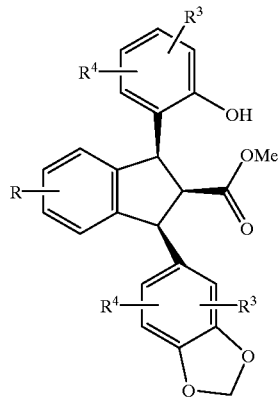

(i)

wherein $R^3$ and $R^4$ are as described in Formula (1) and R is as described in Formula (a).

Prepared in synthesizing the indane carboxylates of Formula (18), preferably Compound (s), are novel intermediates of Formula (1):

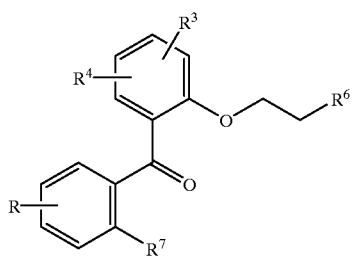

(l)

wherein $R^3$ and $R^4$ are as described in Formula (1), R is as described in Formula (a), $R^6$ is OH or a protected OH and $R^7$ is Br, I, $-OSO_2CF_3$ or $-OSO_2F$.

Also in synthesizing the indane carboxylates of Formula (18), preferably Compound (s), are novel intermediates of Formula (m):

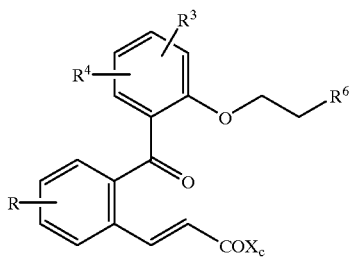

(m)

wherein $R^3$ and $R^4$ are as described in Formula (1), R is as described in Formula (a) and $R^6$ is OH or a protected OH.

Also in synthesizing the indane carboxylates of Formula (18), preferably Compound (s), are novel intermediates of Formula (n):

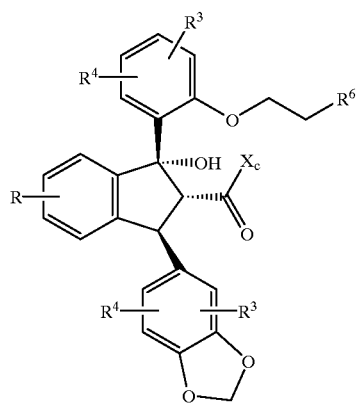

(n)

wherein $R^3$ and $R^4$ are as described in Formula (1), R is as described in Formula (a) and $R^6$ is OH or a protected OH.

Also in synthesizing the indane carboxylates of Formula (18), preferably Compound (s), are novel intermediates of Formula (o):

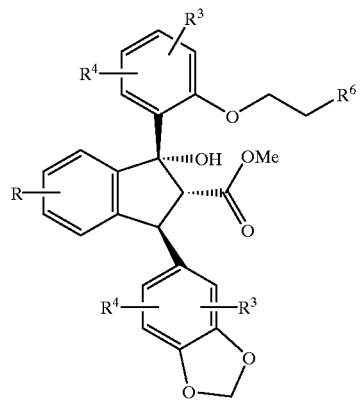

(o)

wherein $R^3$ and $R^4$ are as described in Formula (1), R is as described in Formula (a) and $R^6$ is OH or a protected OH.

Also in synthesizing the indane carboxylates of Formula (18), preferably Compound (s), are novel intermediates of Formula (p):

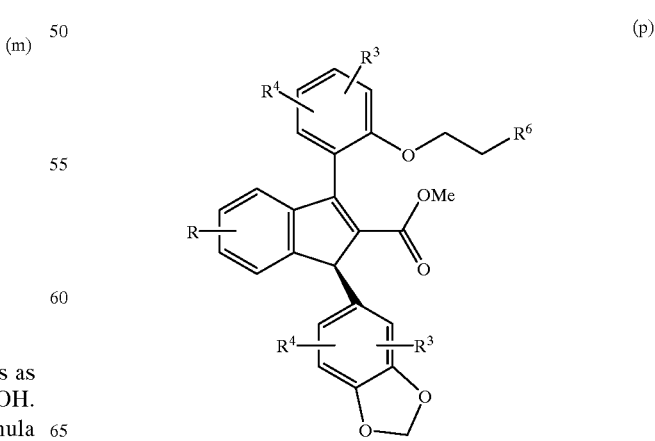

(p)

wherein R³ and R⁴ are as described in Formula (1), R is as described in Formula (a) and R⁶ is OH or a protected OH.

Also in synthesizing the indane carboxylates of Formula (2), preferably Compound (s), are novel racemic intermediates of Formula (28):

(28)

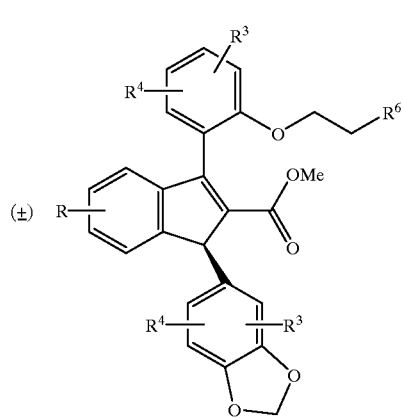

wherein R³ and R⁴ are as described in Formula (1), R is as described in Formula (a) and R⁶ is OH or a protected OH.

Also in synthesizing the indane carboxylates of Formula (18), preferably Compound (s), are novel intermediates of Formula (q):

(q)

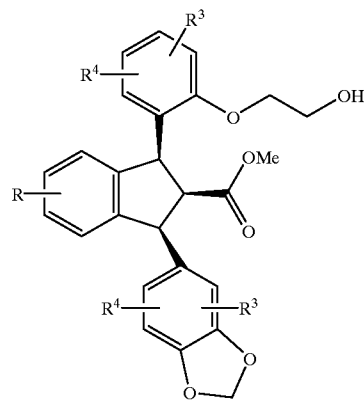

wherein R³ and R⁴ are as described in Formula (1) and R is as described in Formula (a).

Prepared in synthesizing the aromatic ring-fused cyclopentane derivatives of Formula (1) are novel intermediates of Formula (10):

(10)

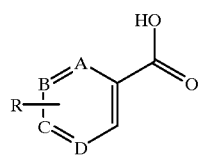

wherein A, B, C and D are carbon atoms or three of A, B, C and D are carbon atoms and one is a nitrogen atom and R is as described in Formula (a).

Prepared in synthesizing the cyclopentano[b]pyridine derivatives of Formula (19) are intermediates of Formula (10) where three of A, B, C and D are carbon atoms and one is a nitrogen atom and R is as described in Formula (a).

Prepared in synthesizing the aromatic ring-fused cyclopentane derivatives of Formula (1) are novel intermediates of Formula (11):

(11)

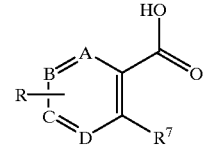

wherein A, B, C and D are carbon atoms or three of A, B, C and D are carbon atoms and one is a nitrogen atom, R is as described in Formula (a) and R⁷ is Br, I, —OSO₂CF₃ or —OSO₂F.

Prepared in synthesizing the cyclopentano[b]pyridine derivatives of Formula (19) are intermediates of Formula (11) where three of A, B, C and D are carbon atoms and one is a nitrogen atom, R is as described in Formula (a) and R⁷ is Br, I, —OSO₂CF₃ or —OSO₂F.

Prepared in synthesizing the aromatic ring-fused cyclopentane derivatives of Formula (1) are novel intermediates of the Formula:

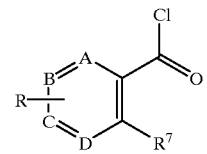

wherein A, B, C and D are carbon atoms or three of A, B, C and D are carbon atoms and one is a nitrogen atom, R is as described in Formula (a) and R⁷ is Br, I, —OSO₂CF₃ or —OSO₂F.

Prepared in synthesizing the cyclopentano[b]pyridine derivatives of Formula (19) are intermediates of the preceding compound where three of A, B, C and D are carbon atoms and one is a nitrogen atom, R is as described in Formula (a) and R⁷ is Br, I, —OSO₂CF₃ or —OSO₂F.

Also prepared in synthesizing the cyclopentano[β] pyridine derivatives of Formula (19) are the novel intermediates of Formula (12):

(12)

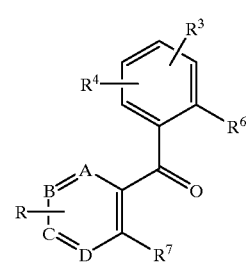

wherein three of A, B, C and D are carbon atoms and one is a nitrogen atom, R³ and R⁴ are as described in Formula (1), R is as described in Formula (a), R⁶ is OH or protected OH and R⁷ is Br, I, —OSO₂CF₃ or —OSO₂F.

Also prepared in synthesizing the cyclopentano[β] pyridine derivatives of Formula (19) are the novel intermediates of Formula (13):

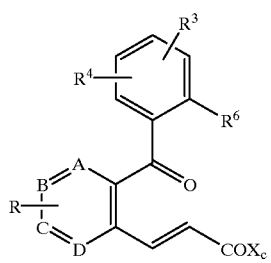
(13)

wherein three of A, B, C and D are carbon atoms and one is a nitrogen atom, $X_c$ is as described above, $R^3$ and $R^4$ are as described in Formula (1), R is as described in Formula (a) and $R^6$ is OH or protected OH.

Also prepared in synthesizing the cyclopentano[β]pyridine derivatives of Formula (19) are the novel intermediates of Formula (14):

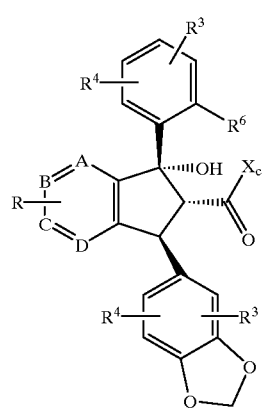
(14)

wherein three of A, B, C and D are carbon atoms and one is a nitrogen atom, $X_c$ is as described above, $R^3$ and $R^4$ are as described in Formula (1), R is as described in Formula (a) and $R^6$ is OH or protected OHd.

Also prepared in synthesizing the cyclopentano[β]pyridine derivatives of Formula (19) are the novel intermediates of Formula (15):

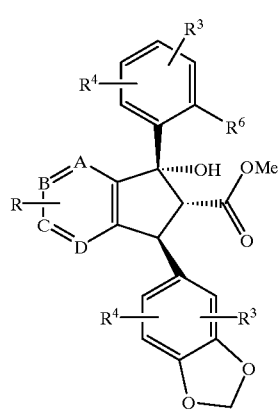
(15)

wherein three of A, B, C and D are carbon atoms and one is a nitrogen atom, $R^3$ and $R^4$ are as described in Formula (1), R is as described in Formula (a) and $R^6$ is OH or protected OH.

Also prepared in synthesizing the cyclopentano[β]pyridine derivatives of Formula (19) are the novel intermediates of Formula (16):

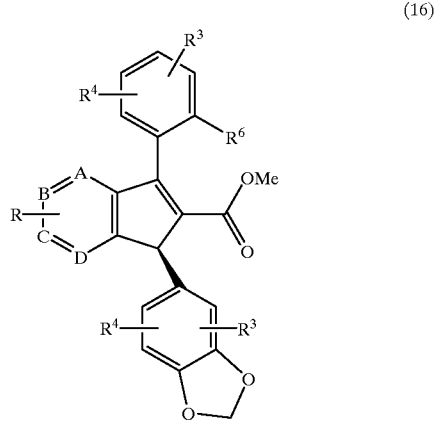
(16)

wherein three of A, B, C and D are carbon atoms and one is a nitrogen atom, $R^3$ and $R^4$ are as described in Formula (1), R is as described in Formula (a) and $R^6$ is OH or protected OH.

Also prepared in synthesizing the cyclopentano[β]pyridine derivatives of Formula (19) are the novel racemic intermediates of Formula (29):

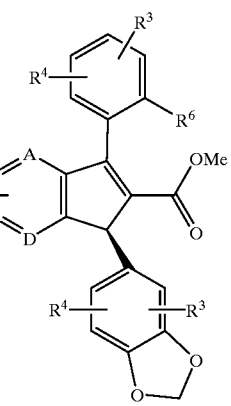
(29)

wherein three of A, B, C and D are carbon atoms and one is a nitrogen atom, $R^3$ and $R^4$ are as described in Formula (1), R is as described in Formula (a) and $R^6$ is OH or protected OH.

Also prepared in synthesizing the cyclopentano[β]pyridine derivatives of Formula (19) are the novel intermediates of Formula (20):

(20)

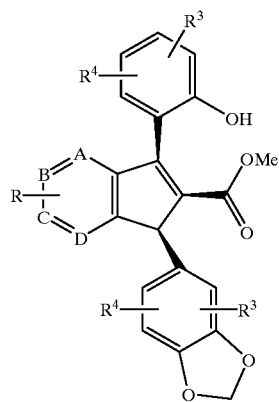

wherein three of A, B, C and D are carbon atoms and one is a nitrogen atom, $R^3$ and $R^4$ are as described in Formula (1) and R is as described in Formula (a).

Also prepared in synthesizing the cyclopentano[β] pyridline derivatives of Formula (19) are the novel intermediates of Formula (21):

(21)

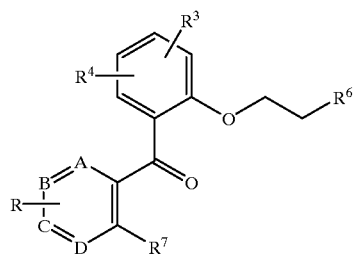

wherein three of A, B, C and D are carbon atoms and one is a nitrogen atom, $R^3$ and $R^4$ are as described in Formula (1), R is as described in Formula (a), $R^6$ is OH or protected OH and $R^7$ is Br, I, —OSO$_2$)CF$_3$ or —OSO$_2$F.

Also prepared in synthesizing the cyclopentano[β] pyridine derivatives of Formula (19) are the novel intermediates of Formula (22):

(22)

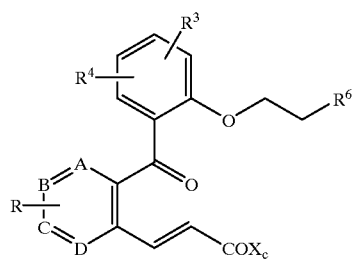

wherein three of A, B, C and D are carbon atoms and one is a nitrogen atom, $X_c$ is as described above, $R^3$ and $R^4$ are as described in Formula (1), R is as described in Formula (a) and $R^6$ is OH or protected OH.

Also prepared in synthesizing the cyclopentano[β] pyridine derivatives of Formula (19) are the novel intermediates of Formula (23):

(23)

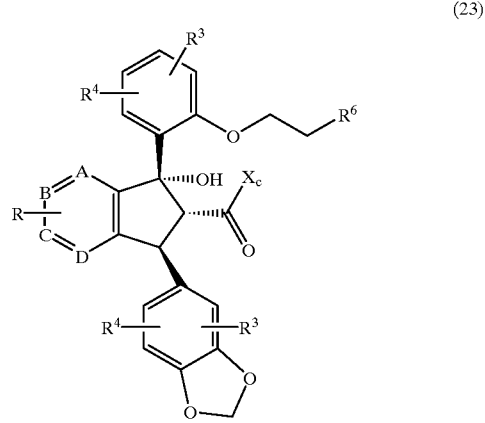

wherein three of A, B, C and D are carbon atoms and one is a nitrogen atom, $X_c$ is as described above, $R^3$ and $R^4$ are as described in Formula (1), R is as described in Formula (a) and $R^6$ is OH or protected OH.

Also prepared in synthesizing the cyclopentano[β] pyridine derivatives of Formula (19) are the novel intermediates of Formula (24):

(24)

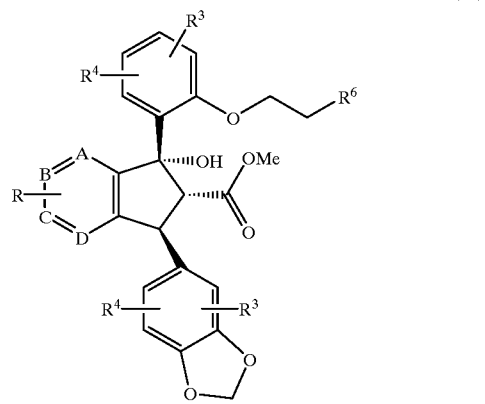

wherein three of A, B, C and D are carbon atoms and one is a nitrogen atom, $R^3$ and $R^4$ are as described in Formula (1), R is as described in Formula (a) and $R^6$ is OH or protected OH.

Also prepared in synthesizing the cyclopentano[β] pyridine derivatives of Formula (19) are the novel intermediates of Formula (25):

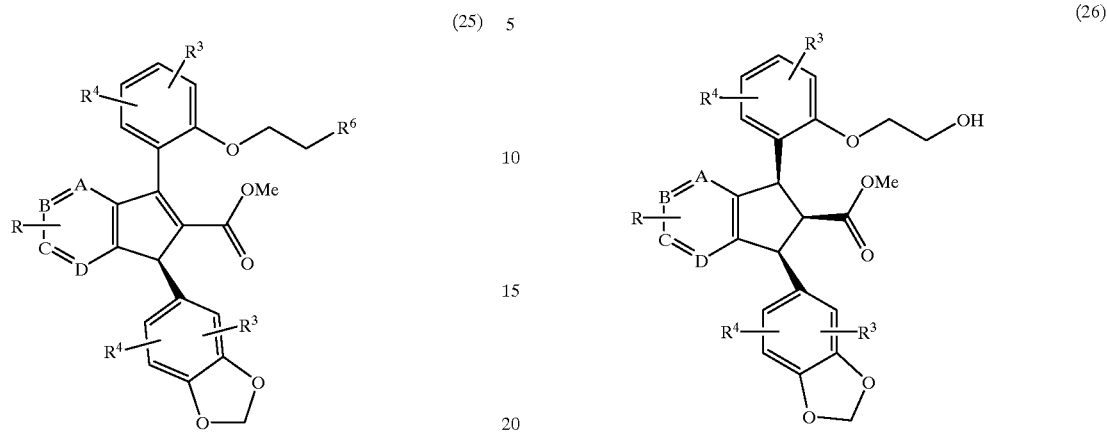

(25)

wherein three of A, B, C and D are carbon atoms and one is a nitrogen atom, $R^3$ and $R^4$ are as described in Formula (1), R is as described in Formula (a) and $R^6$ is OH or protected OH.

Also prepared in synthesizing the cyclopentano[β] pyridine derivatives of Formula (19) are the novel racemic intermediates of Formula (30):

(30)

wherein three of A, B, C and D are carbon atoms and one is a nitrogen atom, $R^3$ and $R^4$ are as described in Formula (1), R is as described in Formula (a) and $R^6$ is OH or protected OH.

Also prepared in synthesizing the cyclopentano[β] pyridine derivatives of Formula (19) are the novel intermediates of Formula (26):

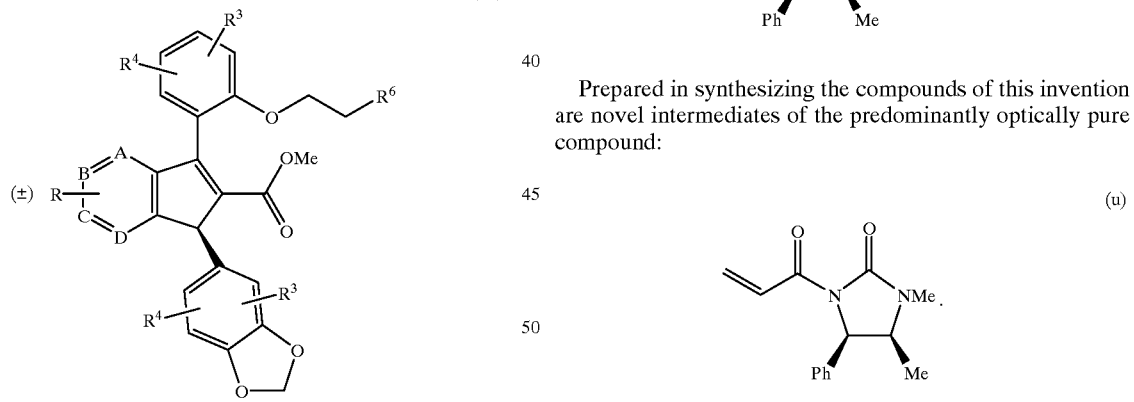

(26)

wherein three of A, B, C and D are carbon atoms and one is a nitrogen atom, $R^3$ and $R^4$ are as described in Formula (1) and R is as described in Formula (a).

Prepared in synthesizing the compounds of this invention are novel intermediates of the predominantly optically pure compound:

(ab)

Prepared in synthesizing the compounds of this invention are novel intermediates of the predominantly optically pure compound:

(u)

All of the starting materials and reagents used herein are known and readily available or can be easily made from known and readily available reagents.

For example, compound (t) is prepared according to the following steps (as used below $R^3$ and $R^4$ are as described in Formula (1)):

a) an appropriately substituted 2-Bromo-5-methoxyphenol, prepared by methods such as described in de Paulis, et al. *J. Med. Chem.*, 28, 1236 (1985), is treated with benzyl bromide and potassium carbonate to form the compound (ad)

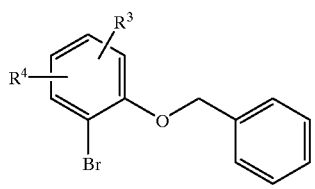

b) treating the product of step a) with magnesium in tetrahydrofuran to form the compound (t)

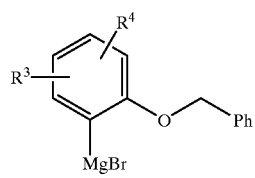

For example, compound (v) is prepared according to the following steps:

c) treating an appropriately substituted 2-Bromo-5-methoxyphenol from step a) above with ethylene carbonate and potassium carbonate in toluene to form the compound (aa)

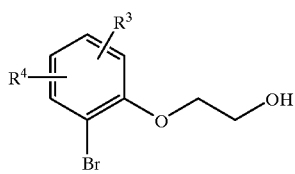

d) treating the product of step c) with potassium carbonate and benzyl chloride in N,N-dimethylformamide to form compound (ae)

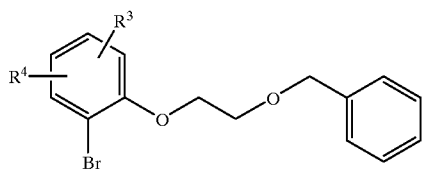

e) treating the product of step d) with magnesium in tetrahydrofuran to form compound (v)

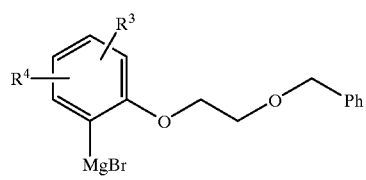

For example, the most preferred compound (u) is prepared according to the following steps:

e) commercially available (1R, 2S)-(−)-ephedrine hydrochloride is reacted with urea and heat to form the compound (ab)

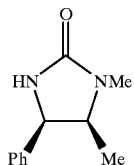

f) treating the product of step e) with acroyl chloride in the presence of base to form compound (u). Preferably, the product of step e) is reacted in the presence of 3-chloropropionyl chloride and a base to form the predominantly optically pure compound (u)

(u)

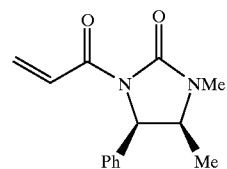

Without further elaboration, it is believed that one skilled in the art can, using the preceding description. utilize the present invention to its fullest extent. The following Examples are, therefore, to be construed as merely illustrative and not a limitation of the scope of the present invention in any way.

EXAMPLES

Example 1

Corresponding to Scheme 1

(+) (1S, 2R, 3S)-3-(2-Carboxymethoxy-4-methoxyphenyl)-1-(3,4-methylenedioxyphenyl)-5-(prop-1-yloxy)indane-2-carboxylic acid disodium salt (i)

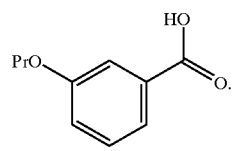

(a compound of Formula (a))

A 12 L 3-necked flask was changed with 500 g (3.62 mol) of 3-hydroxybenzoic acid, 4 L of acetonitrile and 435 g (10.88 mol) of sodium hydroxide in 1.1 L of water. Heated the resulting mix to 60° C. over 40 minutes. Over a 60 minute period the n-dipropyl sulphate (2.5 eq) was added via an addition funnel while maintaining the reaction temperature 65–70° C. After 6 hours a second portion of sodium hydroxide in 1.0 L of H$_2$O was added over 30 minutes within 65–70° C. After another 1.0 L at 65–70° C. the acetonitrile was allowed to evaporate to one half its original volume. 1.0 L of water was added and the pH was adjusted to 3.0 using 850 mL of conc. HCl. 7 L of ethyl acetate was added and the mixture allowed to stir 30 minutes at ambient temperature. At this time the reaction mixture was transferred to a 22 L separatory funnel and 1 L water was added to dissolve inorganic particulates. The organic layer was separated and the organic washed with water (2×4 L) and brine (1×4 L). The solvent was removed until only 600–700 mL remained. 700 mL of hexanes was added and the solution was cooled to 0–5° C. for 3 hours. The solid that precipitated was filtered assay 274 g (1.52 mol). A second crop of 254 g (1.41 mol) was obtained for a total yield of the above depicted compound of 81%; mp 69–71° C.

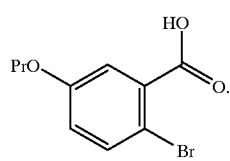

(a compound of Formula (c))

A 22 L. 3-necked flask was charged with 1.037 kg (5.70 mol) of the compound from step (i), 14.2 L of methylene chloride and 579 g of sodium acetate. To this stirred solution was slowly added bromine, keeping the temperature below 34° C. Bromine (1.15 eq) was added until the dark reddish-brown bromine color persisted. Reaction was deemed completed when HPLC monitoring showed starting material was <1.5%. 1.0 L of water and 60 g of sodium bisulfite was added. The solvent was removed until the reaction volume was ~3.0 L. 4 L of ethyl acetate was added and the reaction volume was reduced to 2.5–3 L. 6 L of ethyl acetate was added and the pH was adjusted to ~2 using 300 mL of 50% conc. HCl (v/v). 2 L of water was added the organic layer was separated. The aqueous layer was washed with water (1×4 L) and brine (1×3 L). The solution was reduced to 2 L where upon a white slurry resulted. 800 mL of hexanes was added and the flask was cooled at 0–5° C. for 3 hours with stirring. The solid was collected by filtration to yield the above depicted compound (1171.8 g, 4.5 mol). A second crop was obtained, 189.8 g (0.73 mol) for a total of 5.23 mol, 91% yield, mp 100–102° C.

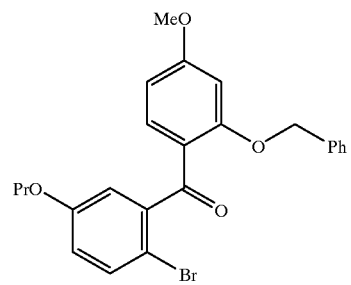

(a compound of Formula (d))

A 3 L, 3-necked flask was charged with 1 kg (3.86 mol) of the compound from step (ii) and thionyl chloride (114.7, 700 mL, 9.62 mol, 2.49 eq) was added all at once. Mixing is endothermic and the reaction temperature drops to 12° C. The slurry is heated to 20–30° C. for 5 and ¾ hours or until the HPLC indicates the disappearance of starting material. The reaction mixture is cooled to ambient temperature and 1 L of toluene is added. The reaction mixture is concentrated by vacuum distillation to about 700 mL and an additional 500 mL toluene was added. Vacuum distillation was continued until 250 mL of toluene was collected.

A 12 L 3-necked flask was charged with the above solution (assume 3.86 mol) and 1,3-dimethoxybenzene (533 g, 3.86 mol). The subsequent solution was cooled to 10° C. and placed under nitrogen atmosphere. Boron trichloride (1 m soln in xylene, 4.2 L, 4.2 mol, 1.088 eq) was added at such a rate that the temperature did not exceed 16° C. Addition takes place over 4 hours, the reaction being 91% complete after addition is complete. The reaction mixture is stirred an additional hour, chilled to 10° C. with an ice bath and quenched carefully with 3 L of water, keeping the temperature below 15° C. The reaction slurry is then heated to 50° C. to dissolve all solids, transferred to a separatory funnel and the organic phase separated, washed with 2×2 L H$_2$O, 1 L 50% brine. The organic solubles are concentrated in vacuo and chased with hexane to produce a crude solid which is recrystallized from 2800 mL 190 proof EtOH. Yield 1202.8 g of the 4-methoxy-2-hydroxy precursor of the title compound (85%, HPLC purity, 97.0% by area).

In a 3 L, 3-necked flask was added 1.5 L of acetonitrile, the above 4-methoxy-2-hydroxy precursor (277.4 g, 0.76 mol), and 214.4 g (1.55 mol) of K2CO3. At room temperature under nitrogen was added benzyl bromide (132.6 g, 0.76 mol). The reaction was heated to reflux (80–81° C.) for 2–4 hours and was followed by HPLC for disappearance of the starting material. The reaction mixture was then cooled to 50° C. and filled to remove inorganics. The solvent was removed under vacuum to yield the above depicted compound as a white solid, 347.0 g (0.762 mol); mp 46–51° C.; yield 100%.

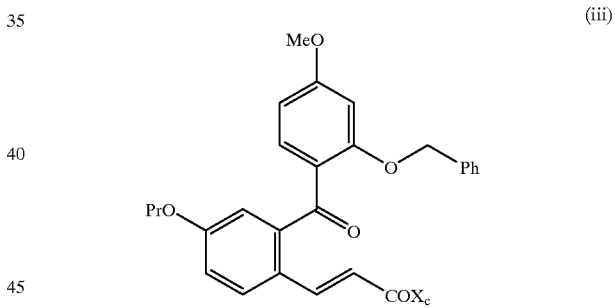

(a compound of Formula (e))

In a 12 L, 3-necked flask was added 600.0 g (1.316 mol) of the compound from step (iii) 312 g of compound (u) (preparation of compound (u) as used in this example is described in the specification on page 33 and in Example 4), 7.4 g of palladium acetate (0.033 mol) 20.2 g of tri-o-tolylphosphine (0.066 mol) 3.3 L of DMF and 107.9 (1.316 mol) of sodium acetate. The reaction mixture was degassed with nitrogen then heated to 135–140° C. The reaction was monitored by HPLC for the disappearance of starting material. The reaction mixture was cooled to 115° C. where 2 L of water and 2 L of toluene were carefully added. The solution was allowed to stir for 7 hours under nitrogen. The reaction solution was warmed to 40–45° C. H$_2$O (3.3 L) and toluene (3.3 L) was added at 50° C. then transferred warm to a 12 L separatory funnel. The separate organic layer was separated and the aqueous layer was washed with water (2×3.3 L). The organic layer was concentrated to yield a wet solid. This material was dissolved in 3.2 L of 190 ethanol.

This solution was cooled to 0–5° C. The precipitated solids were collected via filtration to yield 586 g (0.95 mol, 72%) of the above depicted compound.

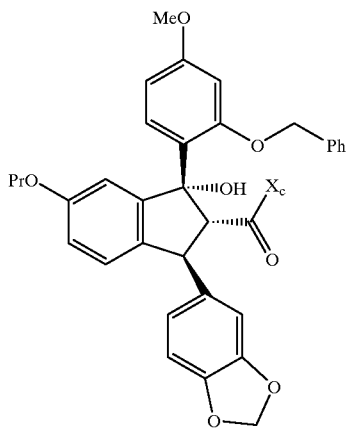

(a compound of Formula (f))

A 3-necked 250 mL flask was charged with cuprous bromide dimethyl sulphide complex (319 g, 019 mol) in 5 mL of THF/Dimethyl sulphide (3/1 ratio v/v). The suspension was cooled to −35° C. and the Grignard (0.04 mol) was added at that temperature. The dark brown suspension was allowed to warm to −5° C. and stir 2–3 minutes then was cooled back down to −35° C. After a total stir time of 35 minutes, the compound from step (iv) (10.0 g, 0.016 mol) dissolved in THF (33 mL) was added over 30 minutes. The reaction was stirred at −35° C. for 2 hours and at −10° C. for one hour. Aqueous amminonium acetate (100 mL of saturated solution) was added at 0° C. and the suspension was stirred at ambient temperature 30 minutes. The organic layer was separated and the aqueous layer was extracted with t-butyl methyl ether (3×100 mL). The combined organic layer was washed with ammonium hydroxide (25% solution) until the blue color no longer persisted. The solvent was removed under vacuum and 50 mL toluene was added then was also removed under vacuum. The residual oil was dissolved in 50 mL of IPA and 150 mL of hexanes was added. The solution was allowed to stir 18 hours at which time a suspension resulted. An additional 150 mL of hexanes was added and the flask was cooled to 0° C. and stirred 30 minutes then filtered. The solid product was dried under vacuum to yield the above depicted compound predominately as the single diastereomer; mp 164–166° C.; 9.72 g (0.013 mol, 81% yield).

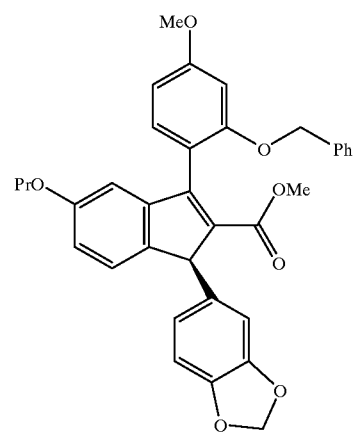

(a compound of Formula (h))

A 2.0 L, 3-necked round-bottomed flask was charged with 1.5 L of toluene and 80.0 g (0.108 mol) of the compound of step (v). The solution was heated to reflux until ~700 mL of solution remained. The solution was then allowed to cool to room temperature under nitrogen. Sodium methoxide 3.0 eq as a 25% solution was slowly added over 10 minutes. The solution was allowed to stir until <1.0% of starting material remained by HPLC. The reaction mixture was cooled to −20° C. then diluted with 200 mL of methanol. The this solution was added 4.5 eq of acetyl chloride (neat) dropwise over 15 minutes keeping the reaction temperature at −10° C. The reaction mixture was allowed to warm to room temperature and stir 1 Hour. It was then diluted with 200 mL TBME and 500 mL of water with vigorous stirring. The organic layer was removed (pH=1) and washed with 20% ethanol (3×600 mL) to remove the chiral auxiliary and yield the above depicted compound predominately as the single enantiomer.

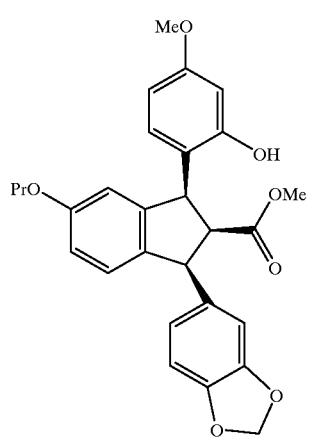

(a compound of Formula (i))

A 150 mL ethyl acetate solution of the compound of step (vi) (30. g, 0.053 mol) was diluted with 100 mL of methanol. To this solution was added 4.0 g of palladium hydroxide on carbon followed by 0.5 mL of concentrated HCI to pH 2–3. The reduction vessel was pressurized to 75 psi and kept ~1.5 hours or until HPLC indicated the disappearance of the starting material. The reaction was filtered and concentrated to yield 18 g (70% yield) of the above depicted compound predominately as the single enantiomer.

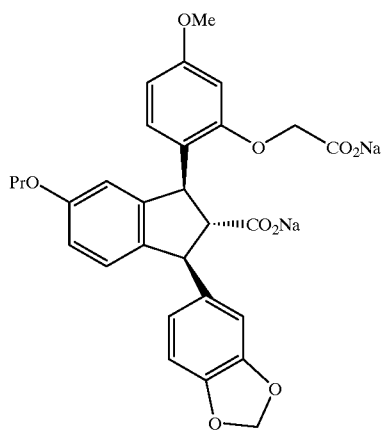

(viii)

(a compound of Formula (k))

A 5 L 3 necked round-bottom flask equipped with an air driven stirrer, and a nitrogen inlet/outlet was charged with 212.0 g (98.4% wt/wt, 437.8 mmol) of the compound of step (vii), 2120 mL of acetone and 212 mL of methanol. The resulting slurry/solution was degassed for approximately 10 minutes under house vacuum. After releasing the vacuum and flushing the flask with nitrogen, 302.5 g (2.19 moles) of potassium carbonate followed by 87.1 g ( 546.6 mol) of methyl bromoacetate were added in single portions. The resulting slurry was stirred at ambient temperature under an atmosphere of nitrogen while the progress of the reaction was monitored by HPLC. The reaction was deemed to be complete when all the starting material had been converted to the title compound. The slurry was filtered through 300 g of Aluminium oxide rinsing with 1250 mL of acetone. The resulting filtrate was concentrated under reduced pressure to a volume of approximately 500 mL. The concentrate was diluted with 2000 mL of t-butyl methyl ether (TBNE) then washed with 2×1000 mL portions of 5% aqueous citric acid followed by 1000 mL of saturated aqueous brine to afford 1720 g of (+)-methyl-(1S,2S,3S)-5-propoxy-1-(3,4-methylenedioxy-phenyl)-3-(2-carbomethoxy]methoxy-4-methoxyphenyl)indane-2-carboxylate (the cis alkylated diester intermediate to the above depicted compound) as a solution in TBNE. Analysis indicated 15.6% wt/wt and 98.5% PAR by HPLC. An analytical sample could be obtained by crystallization of a concentrate from a mixture of hexane's and TBME.

$^1$H NMR (CDCl$_3$), δ7.36 (d, 1 H), 7.07 (d, 1 H), 6.73–6.88 (m, 5 H), 6.49 (q, 1H), 6.37 (d, 1H), 5.94 (s, 2H), 5.17 (d, 1 H), 4.68–4.74 (m, 3 H), 4.02 (t, 1H), 3.90 (t, 2H), 3.81 (s, 3H), 3.75 (s, 3H), 2.97 (s, 3H), 1.75–1.87 (m, 2H), 1.0 (t, 3H ) ppm.

Saponification/epimerization of (+)-methyl-(1S,2S,3S)-5-Propoxy-1-(3,4-methylenedioxy-phenyl)-3-(2-carbomethoxy]methoxy-4-methoxyphenyl)indane-2-carboxylate to (+)-(1S,2R,3S)-5-Propoxy-1-(3,4-methylenedioxy-pheny])-3-(2-carbomethoxy]methoxy-4-methoxyphenyl)indane-2-carboxylic acid was effected by concentration of the TBME solution, dilution with 2-propanol and water and subsequent treatment with an excess of 50% aqueous sodium hydroxide solution (25 equivalents). When the saponification/epimerization was deemed complete, the mixture was acidified with 6N aqueous HCl. Subsequent extractive work-up afforded the diacid intermediate of title compound as a solution in TBMB. Treatment of the diacid with sodium hydroxide afforded the above depicted compound predominately as the single enantiomer.

Example 2

Corresponding to Scheme 2

(+) (1S, 2R, 3S)-3-[2-(2-Hydroxyeth- 1 -yloxy)4-methoxyphenyl]-1-(3,4-methylenedioxyphenyl)-5-(prop-1-yloxy)indane-2-carboxylic acid ethylene diamine salt (2:1)

(i) The title compound was prepared according to Example 1, steps (i) to (vii) by substituting 1-bromo-4-methoxy-2-(2-benzyloxy)ethoxybenzene for 1,3-dimethoxybenzene in step (iii) and utilizing a Grignard reaction in place of the Friedel-Crafts conditions of step (iii) to prepare the mono ester of compound (q), as described in Scheme 2. Saponification/epimerization of the mono ester with lithium hydroxide in TBF afforded the free acid, compound (r) as described on page 7. Compound (r) was treated with ethylene diamine to afford title compound.

Example 3

Corresponding to Scheme 1

(+) (1S, 2R, 3S)-3-[2-(2-Hydroxyeth-1-yloxy)-4-methoxyphenyl]-1-(3,4-methylenedioxyhenyl)-5-(prop-1-yloxy)indane-2-carboxylic acid ethylene diamine salt (2:1)

(i) A 500 mL flask was charged with 150 mL of toluene followed by ethylene carbonate (29.4 g, 98%, 327 mmol) and 15.9 g (97.4%, 32.6 mmol) of methyl-(1S,2S,3S)-1-(3,4-methylenedioxyphenyl)-3-(4-methoxy-2-hydroxyphenyl)-5-propoxyindane-2-carboxylate (a compound of Formula (i) prepared as in step (vii) of Example 1). With moderate agitation at ambient temperature, potassium carbonate (23.1 g, 98%, 163.8 mmol) was added. Under an atmosphere of nitrogen and with moderate agitation, the contents of the flask were heated to approximately 112° C. After approximately 3 hours at or around 112° C., the reaction was cooled to 25–30° C. over a period of 20 minutes, and DI water (120 mL) was added. The mixture was stirred then the aqueous layer was separated. The organic phase was concentrated to a gum under reduced pressure then diluted with methanol (50 mL) and tetrahydrofuran (80 mL). A solution of lithium hydroxide monohydrate, 4.5 g (477.8 mmol) dissolved in 50 mL of water was then added. The reaction mixture was heated to reflux (internal temperature 62–65° C.) over approximately 15 minutes and maintained at reflux while monitoring the reaction progress by HPLC. The reaction was considered complete when no intermediates were detected by HPLC analysis. After approximately 60 minutes at reflux the reaction was considered complete and the contents of the flask cooled to ambient and the reaction mixture concentrated under reduced pressure. Toluene (150 mL), water (150 mL) followed by citric acid (15 g) was then added to the resulting solution and the mixture stirred for approximately 15 minutes. The bottom aqueous layer was drained and the organic layer was washed with aqueous brine solution (100 mL). The organic layer was drained from the flask, then concentrated in vacuo to afford 16.2 g of the free acid of the title compound as a foam. HPLC wt/wt assay indicated 90.5% purity for a corrected yield of 88.8%.

An analytical sample could be obtained by recrystallization from 2-propanol. Mpt. 125–127° C.

(ii) A toluene solution of (+)(1S,2R,3S)]-3-[2-(2-hydroxyeth-1-yloxy)4-methoxyphenyl]-1-(3,4-methylendioxyphenyl)-5-(prop-1-yloxy)indane-2-carboxylic acid (868.8 g @ 11.2% wt/wt, 192.5 mmol) was concentrated under reduced pressure to a volume of approximately 200 mL. Distillation was discontinued and 2-propanol (500 mL) added to the concentrate. The organic solution was concentrated again under reduced pressure to a volume of approximately 200 mL. Distillation was discontinued and 2-propanol (500 mL) added to the concentrate. The resulting solution in 2-propanol was allowed to stir at ambient temperature for approximately 15 minutes to obtain a homogeneous mixture then diluted with an additional 1000 mL of 2-propanol. The resulting solution was heated to approximately 60° C. over a period of 15–20 minutes under a gentle purge of nitrogen. Heating was discontinued and ethylene diamine (11.6 g, 99.5+%, 192.5 mmol) was added. The reaction mixture was cooled to 30–35° C. over a period of 4 hours. As the solution cooled to 57° C., precipitation of the title compound occurred. The resulting slurry was stirred at ambient temperature for approximately 12 hours then cooled to 0° C. an additional 3 hours before isolation of the title compound via filtration. The product was washed with 3 portions of 2-propanol (300 mL) followed by hexane's (600 mL) chilled to 0–5° C. The product was dried in the vacuum oven for approximately 16 hours at 20–25° C. to afford 91.6 (87%) of the title compound. Anal Calcd. for C30H34NO8 C, 67.15; H, 6.39; N, 2.61. Found. C, 67.2; H,6.48; N, 2.67.

Example 4

Chiral Auxiliary

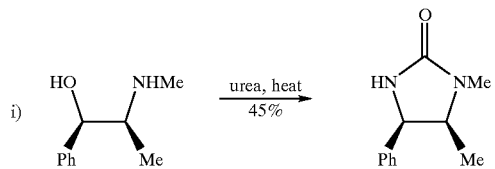

L-ephedrine hydrochlride

To a 3-necked, 12 L round-bottomed flask was charged 5 L of toluene and ephedrine hydrochloride (1.625 hg, 8.06 mol). The flask was heated to 110° C. with mechanical stirring while the solution was being continually purged with nitrogen. Toluene was distilled away using a distillation condenser and the solution was heated to 164–170° C. for 3 hours. HPLC showed the disappearance of most of the product so the reaction mixture was allowed to cool to 120° C. where 4 L of water was added. The mixture was stirred and allowed to cool to room temperature and was filtered. The white solid product was dissolved in 2 L of acetonitrile and concentrated to near dryness where most of the solid product crystallized from solution. The flask was stored in the refrigerator over night at 0° C. The solid was filtered and washed with 15% acetonitrile/water (1 L) and dried in vacuo at 60° C. for 24 hours. The above depicted predominately optically pure compound was obtained as a white solid: 664.8 (43.4% yield); mp 177–179° C.

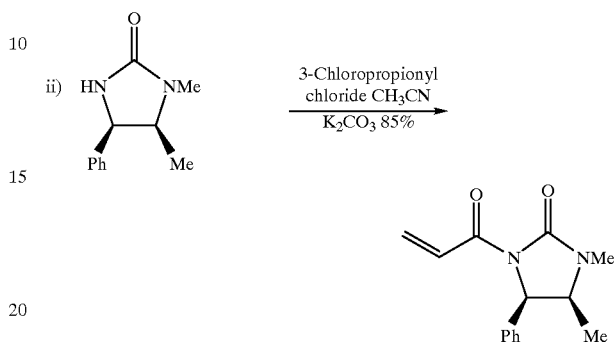

A 5 L, 3-necked flask was charged with 300 g (1.54 mol) of the compound of step i), 3-chloropropionyl chloride (200 mL) and 3 L of acetonitrile. The solution was heated at 75° C. for 8 hours then allowed to cool to room temperature. Potassium carbonate (435 g, 3.15 mol, 2 equiv) was added and the suspension was again heated to 75° C. for 7 hours. The reaction mixture was then cooled to room temperature and filtered. The solvent was removed in vacuo and 680 mL of n-propanol was added and the solvent was cooled to 0° C. and held there for 1 hour. The above depicted predominately optically pure compound was isolated by filtration, washed with hexanes (150 mL), and dried: 326 g (85% yield); mp 149.5–151.0° C.

While the preferred embodiments of the invention are illustrated by the above, it is understood that the invention is not limited to the precise instructions herein disclosed and that the right to all modifications coming within the scope of the following claims is reserved.

What is claimed is:

1. A process for the preparation of the racemic mixture of compounds of Formula (1):

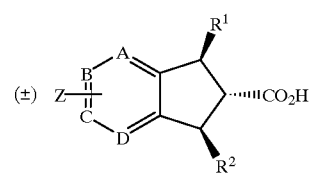

(1)

wherein A, B, C and D are carbon atoms or three of A, B, C and D are carbon atoms and one is a nitrogen atom;

$R^1$ is

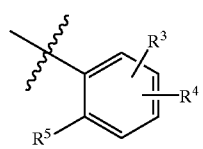

where $R^3$ and $R^4$ are independently H, OH, $C_{1-8}$alkoxy, F, $CF_3$ or $C_{1-6}$alkyl and $R^5$ is —$OCH_2CO_2H$;

$R^2$ is

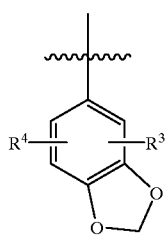

where $R^3$ and $R^4$ are as indicated above and
Z is H, OH, or $C_{1-5}$alkoxy;
or a pharmaceutically acceptable salt thereof, which comprises the steps of:

(1) treating a compound of Formula (10):

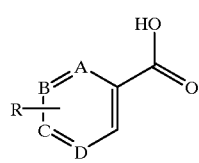
(10)

where A, B, C and D are as described above; and R is H, OH, $C_{1-5}$alkyl of a protected oxy group, in an activation reaction to form a compound of formula (11):

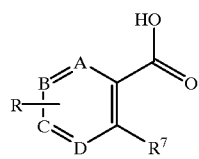
(11)

where A, B, C, D and R are as described above and $R^7$ is Br, I, $—OSO_2CF_3$ or $—OSO_2F$;

(2) reacting the product of step (1) with an acid chloride to form a compound of the formula

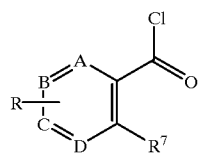

where A, B, C, D, R and $R^7$ are as defined above;
and a compound of the Formula:

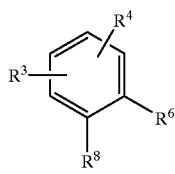

where $R^3$ and $R^4$ are as described above, $R^6$ is OH or protected OH and $R^8$ is MgBr or H, to form a compound of Formula (12):

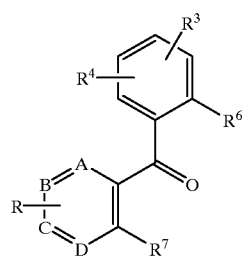
(12)

where A, B, C, D, R, $R^3$, $R^4$ and $R^6$ as defined above and $R^7$ is Br, I, $—OSO_2CF_3$ or $—OSO_2F$;

(3) reacting the product of step (2) with the compound

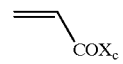

wherein $X_c$ is an achiral group;

in the presence of a catalyst to form a compound of formula (13):

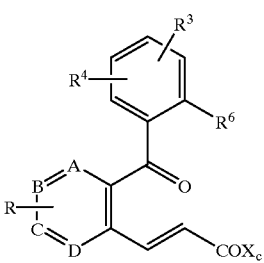
(13)

where A, B, C, D, R, $R^3$, $R^4$, $R^6$ and $X_c$ are as defined above;

(4) treating the product of step (3) with a compound of the formula:

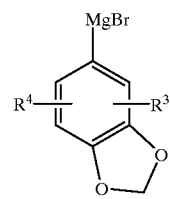

where $R^3$ and $R^4$ are as defined above, with copper complex to form a compound of the Formula:

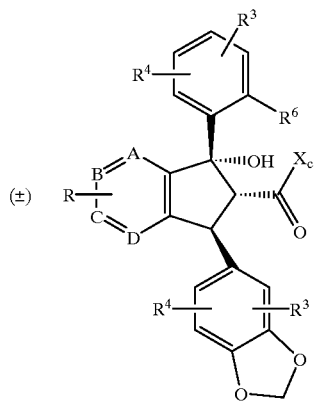

(±)

where A, B, C, D, R, R³, R⁴, R⁶ and X_c are as defined above:

(5) treating the product of step (4) with sodium methoxide in methanol to form a compound of the Formula:

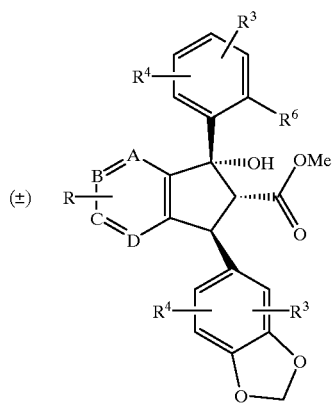

(±)

where A, B, C, D, R, R³, R⁴ and R⁶ are as defined above;

(6) treating the product of step (5) under acidic conditions to form a compound of the Formula:

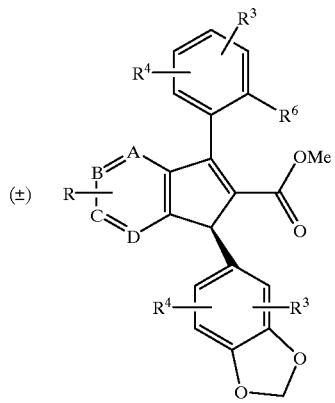

(±)

where A, B, C, D, R, R³, R⁴ and R⁶ are as defined above;

(7) hydrogenating the product of step (6) over palladium to form a compound of Formula (29):

(29)

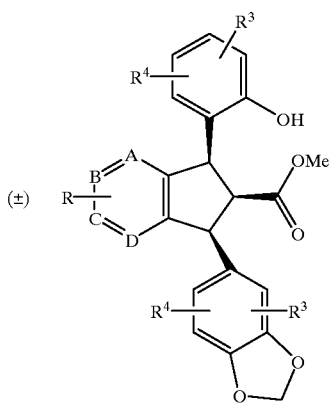

(±)

where A, B, C, D, R, R³ and R⁴ are as defined above;

(8) treating the product of step (7) with methyl bromoacetate, potassium carbonate in acetone/methanol, followed by saponification with lithium hydroxide monohydrate and acidic workup to form a compound of the Formula:

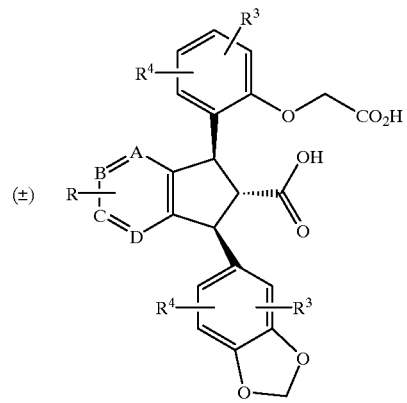

(±)

where A, B, C, D, R, R³ and R⁴ are as defined above;

(9) treating the product of step (8) with sodium hydroxide to form the final product, the compound

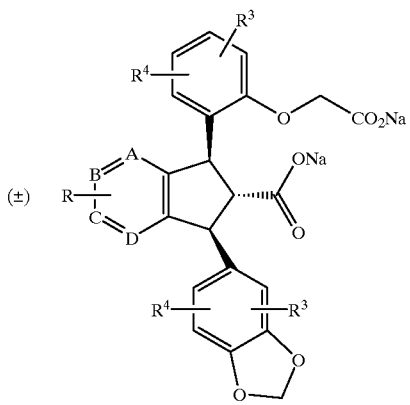

(±)

where A, B, C, D, R, R³ and R⁴ are as defined above.

2. A process for the preparation of the racemic mixture of compounds of Formula (1):

(1)

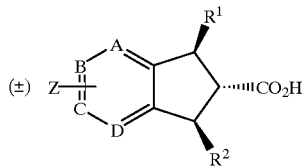

wherein A, B, C and D are carbon atoms or three of A, B, C and D are carbon atoms and one is a nitrogen atom;

$R^1$ is

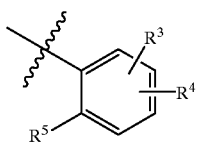

where R and $R^4$ are independently H, OH, $C_{1-8}$alkoxy, F, $CF_3$ or $C_{1-6}$alkyl and $R^5$ is $-OCH_2CH_2OH$;

$R^2$ is

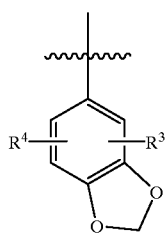

where $R^3$ and $R^4$ are as indicated above and

Z is H, OH, or $C_{1-5}$alkoxy;

or a pharmaceutically acceptable salt thereof, which comprises the steps of:

(1) reacting the compound (11):

(11)

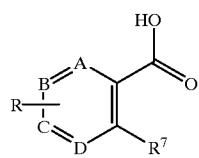

where A, B, C and D are as described above, R is H, OH, $C_{1-5}$alkyl of a protected oxy group and $R^7$ is Br, I, $-OSO_2CF_3$ or $-OSO_2F$;

with an acid chloride to form a compound of the formula

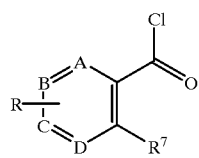

where A, B, C, D, R and $R^7$ are as defined above;

and a compound of the formula:

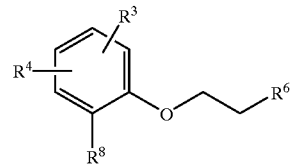

where $R^3$ and $R^4$ are as described above, $R^6$ is OH or protected OH and $R^8$ is MgBr, to form a compound of Formula (21)

(21)

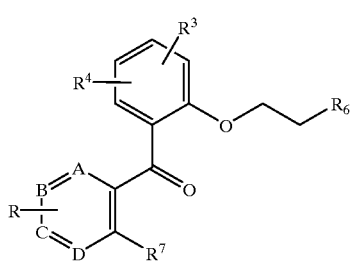

where A, B, C, D, R, $R^3$, $R^4$ and $R^6$ are as described above and $R^7$ is Br, I, $-OSO_2CF_3$ or $-OSO_2F$;

(2) reacting the product of step (1) with the compound

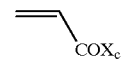

wherein $X_c$ is an achiral group;

in the presence of a catalyst to form a compound of formula (22):

(22)

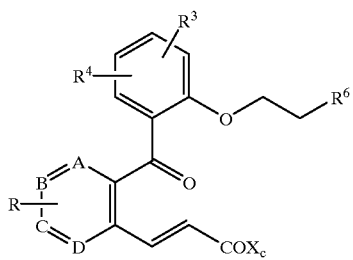

where A, B, C, D, R, $R^3$, $R^4$, $R^6$ and $X_c$ are as defined above;

(3) treating the product of step (2) with a compound of the formula:

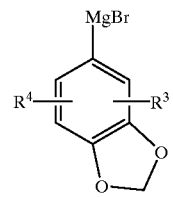

where $R^3$ and $R^4$ are as defined above, with copper complex to form a compound of the Formula:

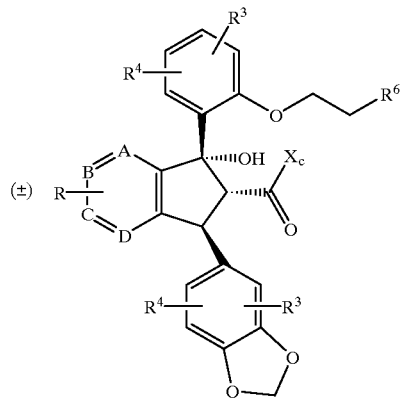

where A, B, C, D, R, R³, R⁴, R⁶ and $X_c$ are as defined above;

(4) treating the product of step (3) with sodium methoxide in methanol to form a compound of the Formula:

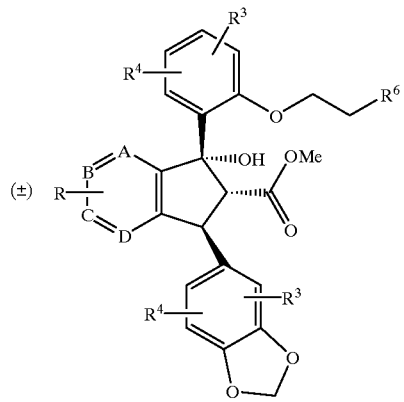

where A, B, C, D, R, R³, R⁴ and R⁶ are as defined above;

(5) treating the product of step (4) under acidic conditions to form a compound of the Formula:

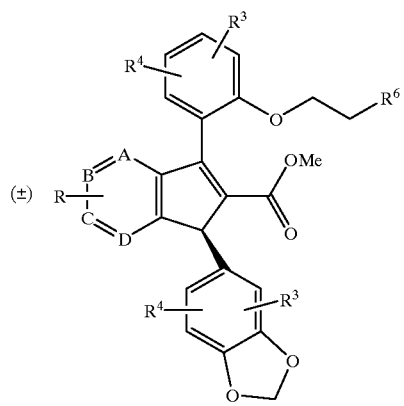

where A, B, C, D, R, R³, R⁴ and R⁶ are as defined above;

(6) hydrogenating the product of step (5) over palladium to form a compound of Formula:

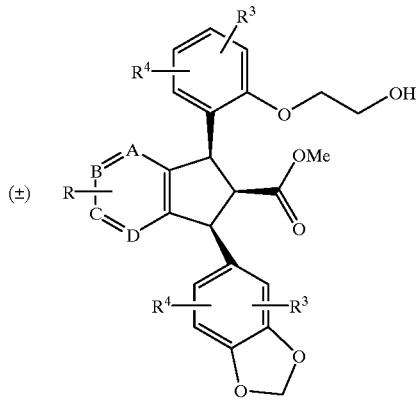

where A, B, C, D, R, R³ and R⁴ are as defined above;

(7) treating the product of step (6) with lithium hydroxide monohydrate to effect saponification and epimerization followed by acidic workup to form a compound of the Formula:

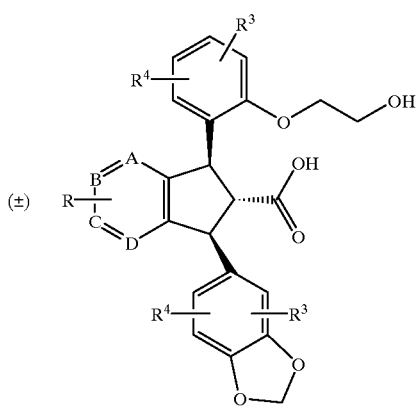

where A, B, C, D, R, R³ and R⁴ are as defined above;

(8) treating the product of step (7) with ethylene diamine to form the final product, the compound

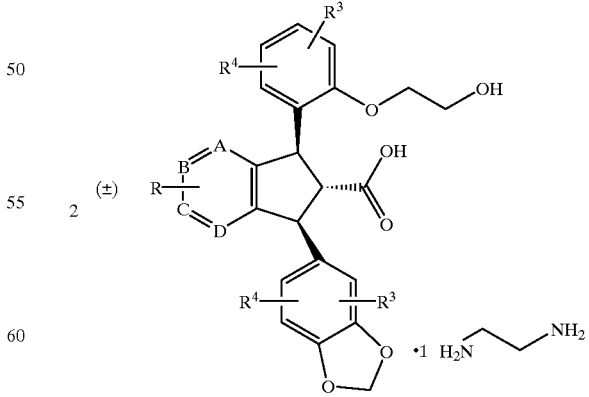

where A, B, C, D, R, R³ and R⁴ are as defined above.

3. A process of claim 1 for the preparation of a compound of the Structure (k)

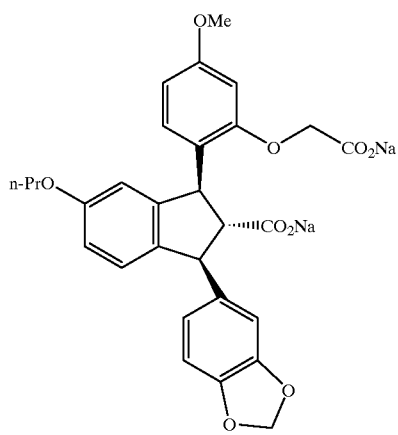

(k)

comprising the steps of
(1) treating a compound of the formula

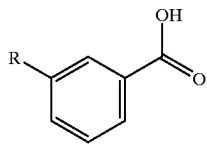

where R is as defined in claim 1, in an activation reaction to form a compound of the formula

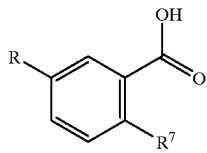

where R and $R^7$ is as defined in claim 1;
(2) treating the product of step (1) with an acid chloride to form a compound of the formula;

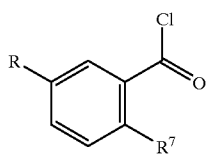

where R and $R^7$ is as defined in claim 1;
(3) reacting the product of step (2) in an acylation reaction with a compound of the formula

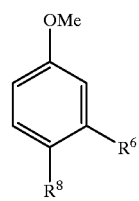

where $R^8$ is MgBr and $R^6$ is benzyl or $R^8$ is H and $R^6$ OMe, to form a compound of the formula

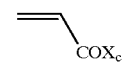

where R and $R^7$ are as defined in claim 1;

(4) reacting the product of step (3) with the compound (u)

$$\text{COX}_c$$

wherein $X_c$ is (ac)

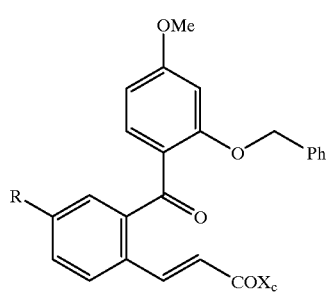

in the presence of a palladium catalyst to form a compound of the formula (e)

where R is as defined in claim 1 and $X_c$ is as indicated above;

(5) treating the product of step (4) with 3,4-(methylenedioxy)phenylmagnesium bromide and a copper complex to form a compound of the formula

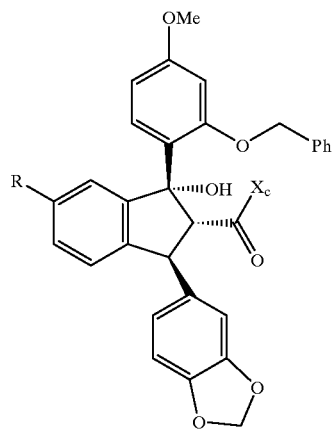
(f)

where R is as defined in claim 1;
(6) treating the product of step (5) with sodium methoxide in methanol to form a compound of the formula

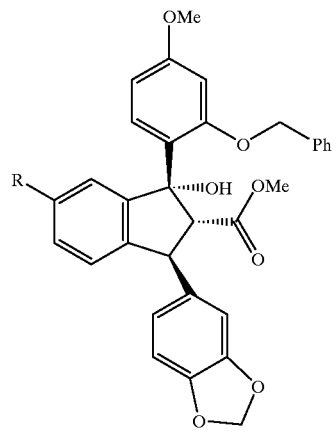
(g)

where R is as defined in claim 1;
(7) treating the product of step (6) under acidic conditions to form a compound of the formula

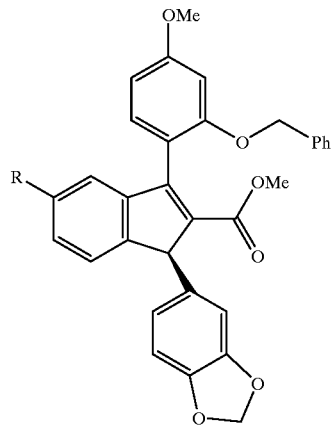
(h)

where R is as defined in claim 1;
(8) hydrogenating the product of step (7) over palladium on carbon to form the compound

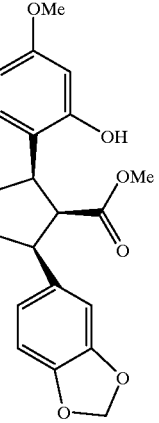
(i)

where R is as defined in claim 1;
(9) treating the product of step (8) with methyl bromoacetate, potassium carbonate in acetone/methanol, followed by saponification with lithium hydroxide monohydrate and acidic workup to form the compound (j)

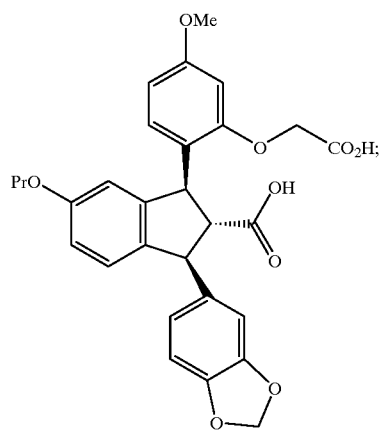

(10) treating the product of step (9) with sodium hydroxide to form the final product, the compound (k)

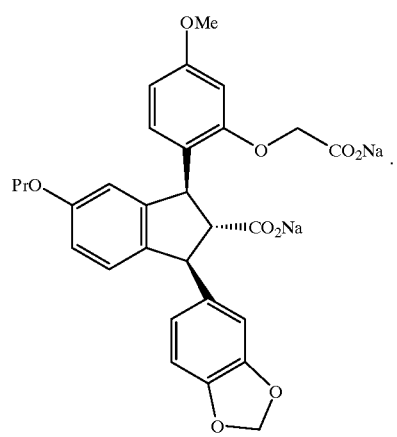

4. A process of claim 2 for the preparation of a compound of the Structure (s)

(s)

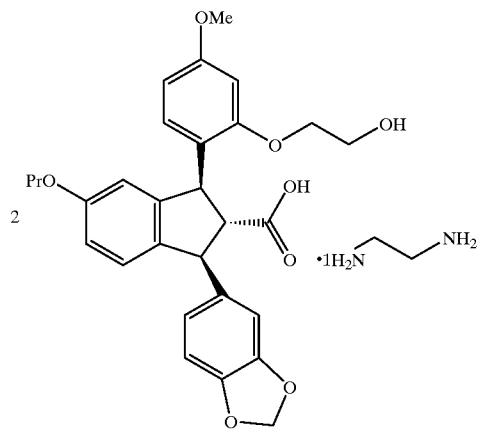

comprising the steps of (1) reacting the a compound of the formula

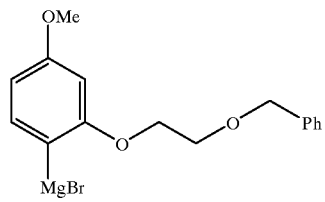

where R and $R^7$ are as described in claim 3, with the compound (v)

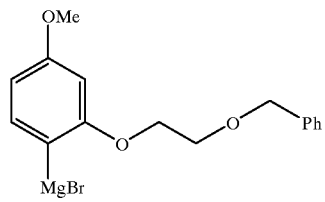

to form the compound (l)

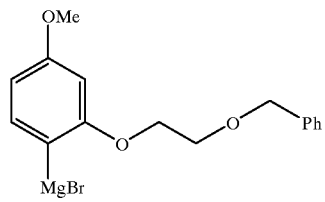

(2) reacting the product of step (1) with the compound (u)

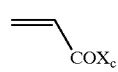

wherein $X_c$ is (ac)

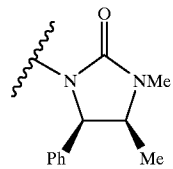

in the presence of a palladium catalyst to form a compound of the formula (m)

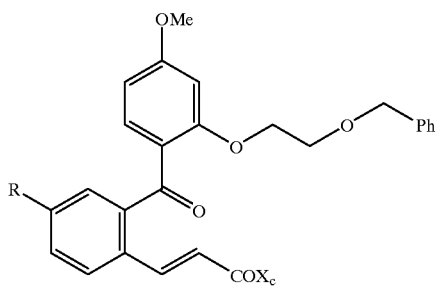

where R is as described in claim 1;

(3) treating the product of step (2) with 3,4-(methylenedioxy)phenylmagnesium bromide and a copper complex to form a compound of the formula (n)

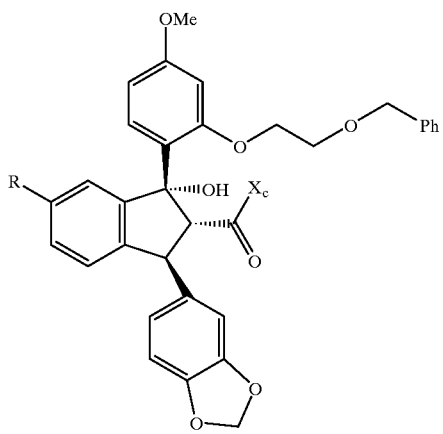

where R is as described in claim 1;

(4) treating the product of step (3) with sodium methoxide in methanol to form a compound of the formula (o)

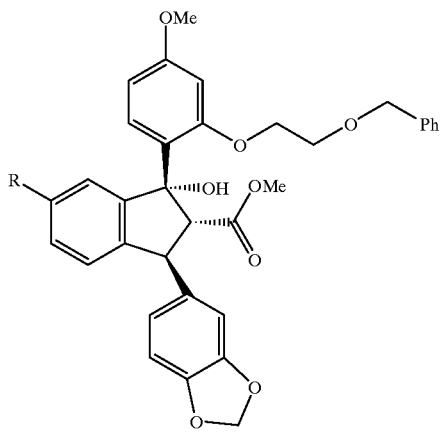

where R is as described in claim 1;

(5) treating the product of step (4) under acidic conditions to form a compound of the formula (p)

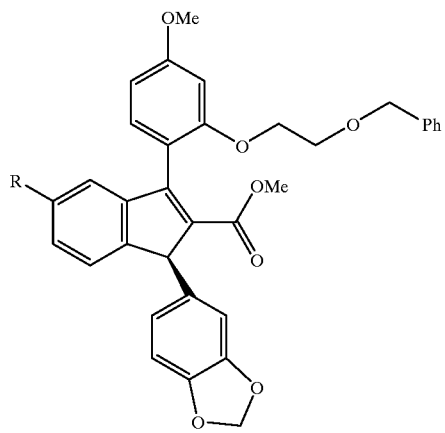

where R is as described in claim 1;

(6) hydrogenating the product of step (5) over palladium to form a compound of the formula (q)

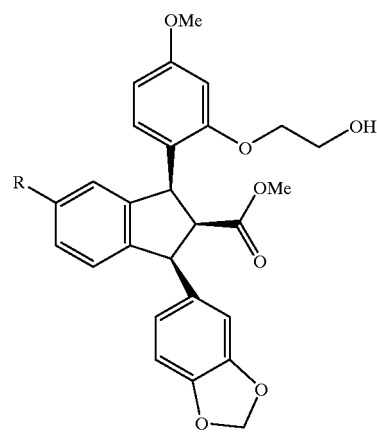

where R is as described in claim 1;

(7) treating the product of step (6) with lithium hydroxide monohydrate, followed by the acidic workup to form the compound (r)

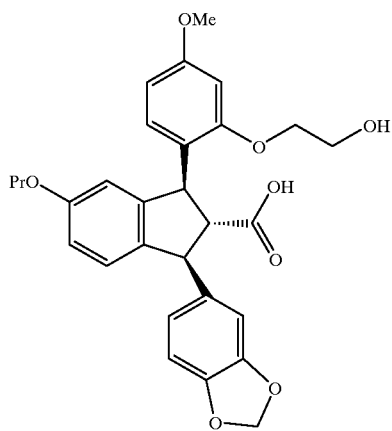

(8) treating the product of step (7) with ethlenediamine to form the final product, the compound (s)

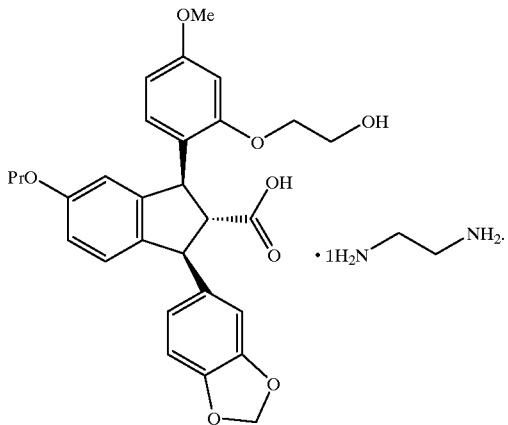

5. A process of claim 1 for the preparation of compounds of Formula (19):

(19)

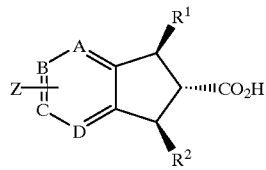

wherein three of A, B, C and D are carbon atoms and one is a nitrogen atom, $R^1$ is

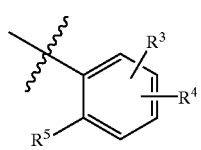

where $R^3$ and $R^4$ are independently H, OH, $C_{1-8}$alkoxy, F, $CF_3$ or $C_{1-6}$alkyl and $R^5$ is —$OCH_2CO_2H$;

$R^2$ is

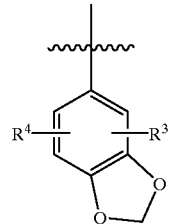

where $R^3$ and $R^4$ are as indicated above and
Z is H, OH, or $C_{1-5}$alkoxy;

or a pharmaceutically acceptable salt thereof, which comprises the steps of:

(1) treating a compound of Formula (10):

(10)

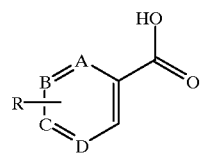

where A, B, C and D are as described above; and R is H, OH, $C_{1-5}$alkyl of a protected oxy group, in an activation reaction to form a compound of the formula:

(11)

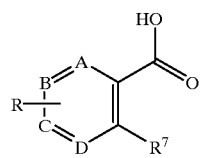

where A, B, C, D and R are as described above and $R^7$ is Br, I, —$OSO_2CF_3$ or —$OSO_2F$;

(2) reacting the product of step (1) with an acid chloride to form a compound of the formula

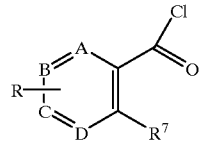

where A, B, C, D, R and $R^7$ are as defined above, and a compound of Formula (t):

(t)

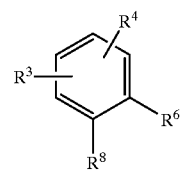

where $R^3$ and $R^4$ are as described above, $R^6$ is OH or protected OH and $R^8$ is MgBr or H, to form a compound of Formula (12):

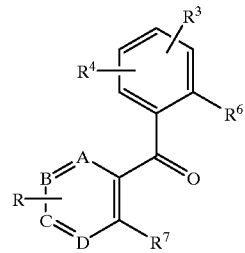

where A, B, C, D, R, $R^3$, $R^4$ and $R^6$ as defined above and $R^7$ is Br, I, $-OSO_2CF_3$ or $-OSO_2F$;

(3) reacting the product of step (2) with the compound

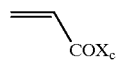

(u)

wherein $X_c$ is

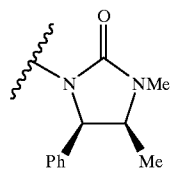

(ac)

in the presence of a palladium catalyst to form a compound of the formula:

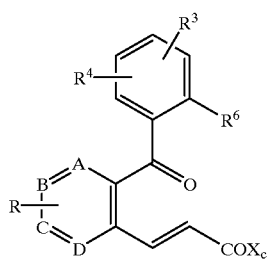

(13)

where A, B, C, D, R, $R^3$, $R^4$, $R^6$ and $X_c$ are as defined above;

(4) treating the product of step (3) with a compound of the formula:

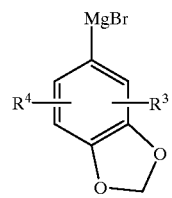

where $R^3$ and $R^4$ are as defined above, with copper complex to form a compound of the Formula (14):

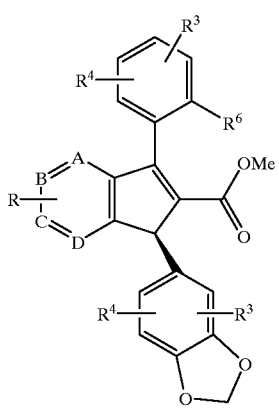

(14)

where A, B, C, D, R, $R^3$, $R^4$, $R^6$ and $X_c$ are as defined above;

(5) treating the product of step (4) with sodium methoxide in methanol to form a compound of the Formula (15):

(15)

where A, B, C, D, R, $R^3$, $R^4$ and $R^6$ are as defined above;

(6) treating the product of step (5) under acidic conditions to form a compound of the Formula (16):

(16)

where A, B, C, D, R, $R^3$, $R^4$ and $R^6$ are as defined above;

(7) hydrogenating the product of step (6) over palladium to form a compound of Formula (20):

(20)

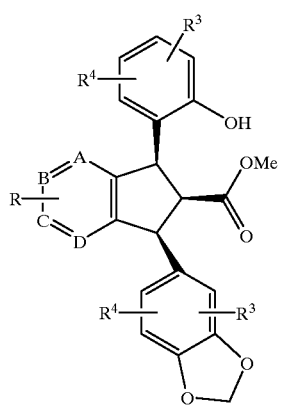

where A, B, C, D, R, $R^3$ and $R^4$ are as defined above;

(8) treating the product of step (7) with methyl bromoacetate, potassium carbonate in acetone/methanol, followed by saponification with lithium hydroxide monohydrate and acidic workup to form a compound of the Formula:

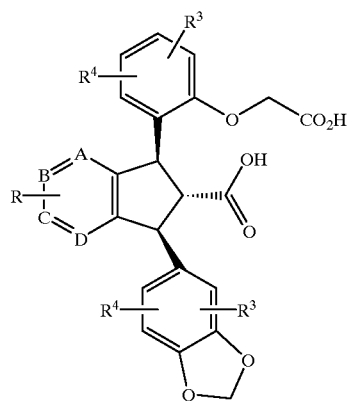

where A, B, C, D, R, $R^3$ and $R^4$ are as defined above;

(9) treating the product of step (8) with sodium hydroxide to form the final product, the compound

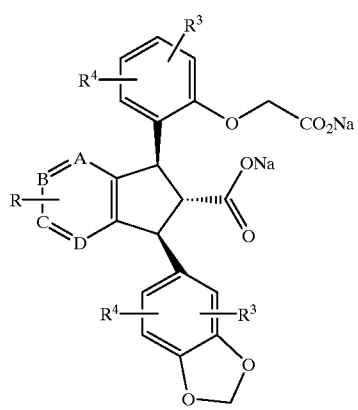

where A, B, C, D, R, $R^3$ and $R^4$ are as defined above, predominantly as the single enantiomer depicted.

6. A process of claim 2 for the preparation of compounds of Formula (19):

(19)

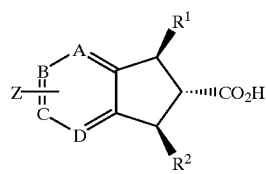

wherein three of A, B, C and D are carbon atoms and one is a nitrogen atom;

$R^1$ is

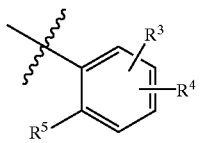

where $R^3$ and $R^4$ are independently H, OH, $C_{1-8}$alkoxy, F, $CF_3$ or $C_{1-6}$alkyl and $R^5$ is $-OCH_2CH_2OH$;

$R^2$ is

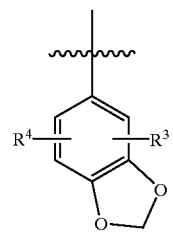

where $R^3$ and $R^4$ are as indicated above and

Z is H, OH, or $C_{1-5}$alkoxy;

or a pharmaceutically acceptable salt thereof, which comprises the steps of:

(1) reacting the compound (11):

(11)

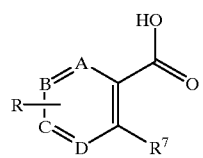

where A, B, C and D are as described above, R is H, OH, $C_{1-5}$alkyl or a protected oxy group and $R^7$ is Br, I, $-OSO_2CF_3$ or $-OSO_2F$;

with an acid chloride to form a compound of the formula

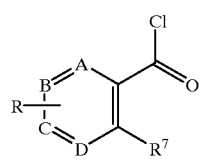

where A, B, C, D, R and $R^7$ are as defined above;

and a compound of the formula:

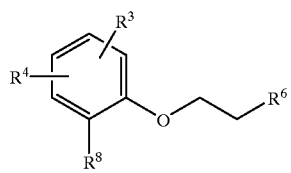

where $R^3$ and $R^4$ are as described above, $R^6$ is OH or protected OH and $R^8$ is MgBr, to form a compound of Formula (21)

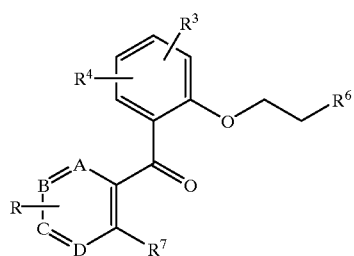

(21)

where A, B, C, D, R, $R^3$, $R^4$ and $R_6$ are as described above and $R^7$ is Br, I, $-OSO_2CF_3$ or $-OSO_2F$, (2) reacting the product of step (1) with the compound

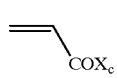

(u)

wherein $X_c$ is

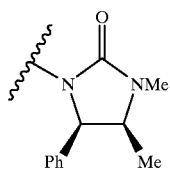

(ac)

in the presence of a catalyst to form a compound of formula (22):

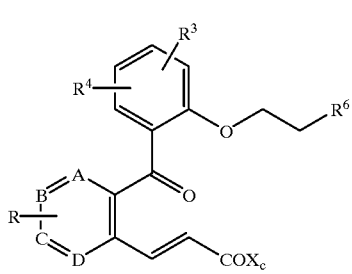

(22)

where A, B, C, D, R, $R^3$, $R^4$, $R^6$ and $X_c$ are as defined above;
(3) treating the product of step (2) with a compound of the formula:

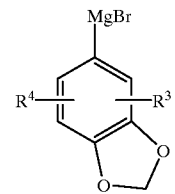

where $R^3$ and $R^4$ are as defined above, with copper complex to form a compound of the Formula (23):

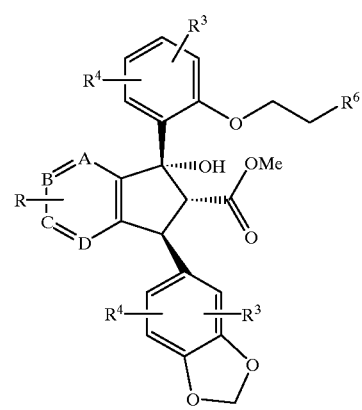

(23)

where A, B, C, D, R, $R^3$, $R^4$, $R^6$ and $X_c$ are as defined above;

(4) treating the product of step (3) with sodium methoxide in methanol to form a compound of the Formula (24):

(24)

where A, B, C, D, R, $R^3$, $R^4$ and $R^6$ are as defined above;

(5) treating the product of step (4) under acidic conditions to form a compound of the Formula (25):

(25)

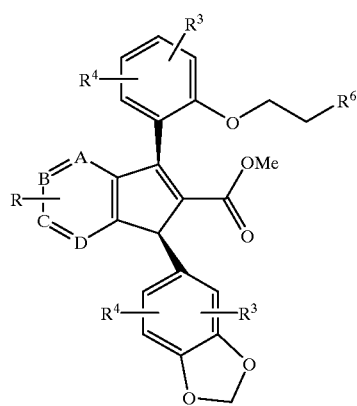

where A, B, C, D, R, $R^3$, $R^4$ and $R^6$ are as defined above;
(6) hydrogenating the product of step (5) over palladium to form a compound of Formula (26):

(26)

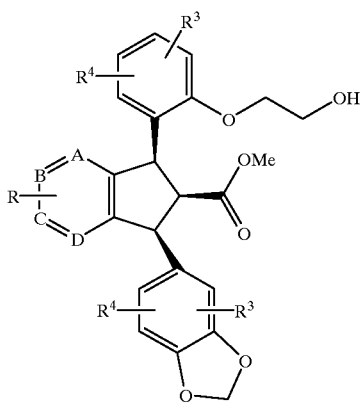

where A, B, C, D, R, $R^3$, $R^4$ and $R^6$ are as defined above;
(7) treating the product of step (6) with lithium hydroxide monohydrate to effect saponification and epimerization followed by an acidic workup to form a compound of the Formula:

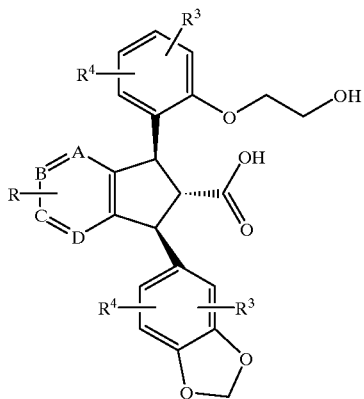

where A, B, C, D, R, $R^3$ and $R^4$ are as defined above;

(8) treating the product of step (7) with ethylene diamine to form the final product, the compound

2

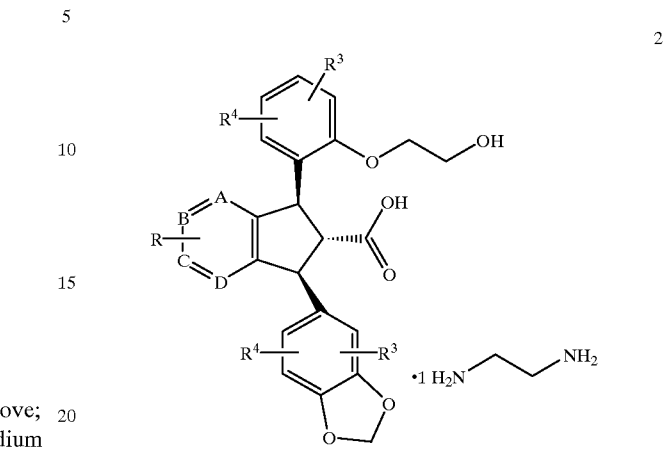

where A, B, C, D, R, $R^3$ and $R^4$ are as defined above, predominantly as the single enantiomer depicted.

7. A process for the preparation of a compound as described in claim 1, step (8), or a pharmaceutically acceptable salt thereof, which comprises converting a compound of the formula,

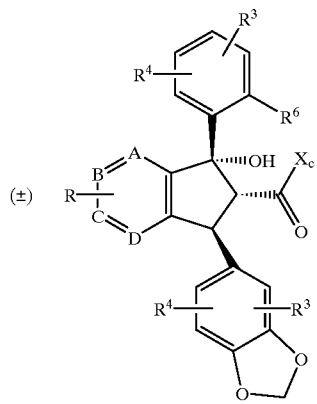

wherein A, B, C, D, R, $R^3$, $R^4$, $R^6$ and $X_c$ are as described in claim 1, into a compound as described in claim 1, step (8), and thereafter optionally forming a pharmaceutically acceptable salt thereof.

8. A process for the preparation of a compound as described in claim 1, step (8), or a pharmaceutically acceptable salt thereof, which comprises converting a compound of the formula, wherein A, B, C, D, R, R³, R⁴ and R⁶ are as described in claim 1, into a compound as described in claim 1, step (8), and thereafter optionally forming a pharmaceutically acceptable salt thereof.

9. A process for the preparation of a compound as described in claim 1, step (8), or a pharmaceutically acceptable salt thereof, which comprises converting a compound of the formula, wherein A, B, C, D, R, R³, R⁴ and R⁶ are as defined in claim 1, into a compound as described in claim 1, step (8), and thereafter optionally forming a pharmaceutically acceptable salt thereof.

10. A process for the preparation of a compound as described in claim 2, step (7), or a pharmaceutically acceptable salt thereof, which comprises converting a compound of the formula, wherein A, B, C, D, R, R³, R⁴, R⁶ and $X_c$ are as defined in claim 2, into a compound as described in claim 2, step (7), and thereafter optionally forming a pharmaceutically acceptable salt thereof.

11. A process for the preparation of a compound as described in claim 2, step (7), or a pharmaceutically acceptable salt thereof, which comprises converting a compound of the formula, wherein A, B, C, D, R, R³, R⁴ and R⁶ are as defined in claim 2, into a compound as described in claim 2, step (7), and thereafter optionally forming a pharmaceutically acceptable salt thereof.

12. A process for the preparation of a compound as described in claim 2, step (7), or a pharmaceutically acceptable salt thereof, which comprises converting a compound of the formula,

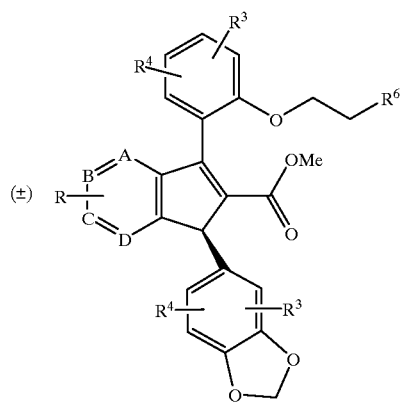

wherein A, B, C, D, R, $R^3$, $R^4$ and $R^6$ are as defined in claim 2, into a compound as described in claim 2, step (7), and thereafter optionally forming a pharmaceutically acceptable salt thereof.

13. A process for the preparation of a compound of formula (j), as described in claim 3, step (9), or a pharmaceutically acceptable salt thereof, which comprises converting a compound of the structure,

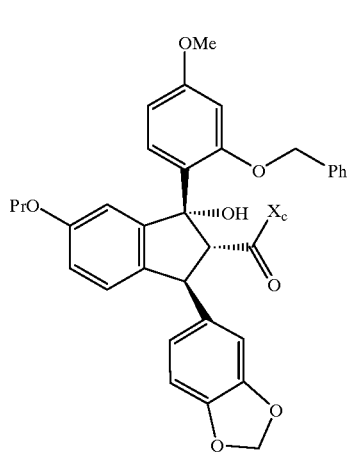

predominantly as the single diastereomer depicted, into a compound of formula (j), as described in claim 3, step (9), and thereafter optionally forming a pharmaceutically acceptable salt thereof.

14. A process for the preparation of a compound of formula (j), as described in claim 3, step (9), or a pharmaceutically acceptable salt thereof, which comprises converting a compound of the structure,

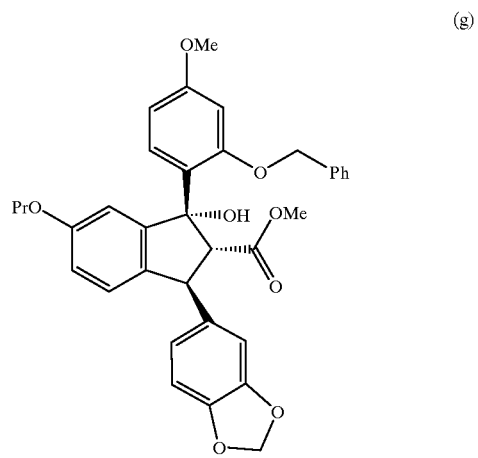

predominantly as the single enantiomer depicted, into a compound of formula (j), as described in claim 3, step (9), and thereafter optionally forming a pharmaceutically acceptable salt thereof.

15. A process for the preparation of a compound of formula (j), as described in claim 3, step (9), or a pharmaceutically acceptable salt thereof, which comprises converting a compound of the structure,

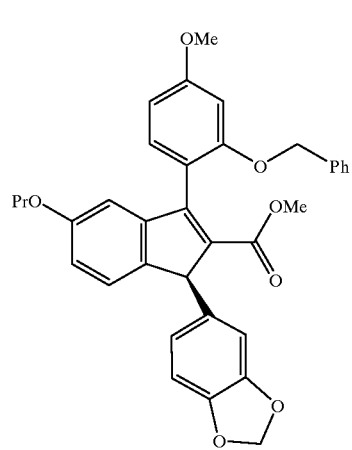

predominantly as the single enantiomer depicted, into a compound of formula (j), as described in claim 3, step (9), and thereafter optionally forming a pharmaceutically acceptable salt thereof.

16. A process for the preparation of a compound of formula (r), as described in claim 4, step (7), or a pharmaceutically acceptable salt thereof, which comprises converting a compound of the structure, ing a compound of the structure,

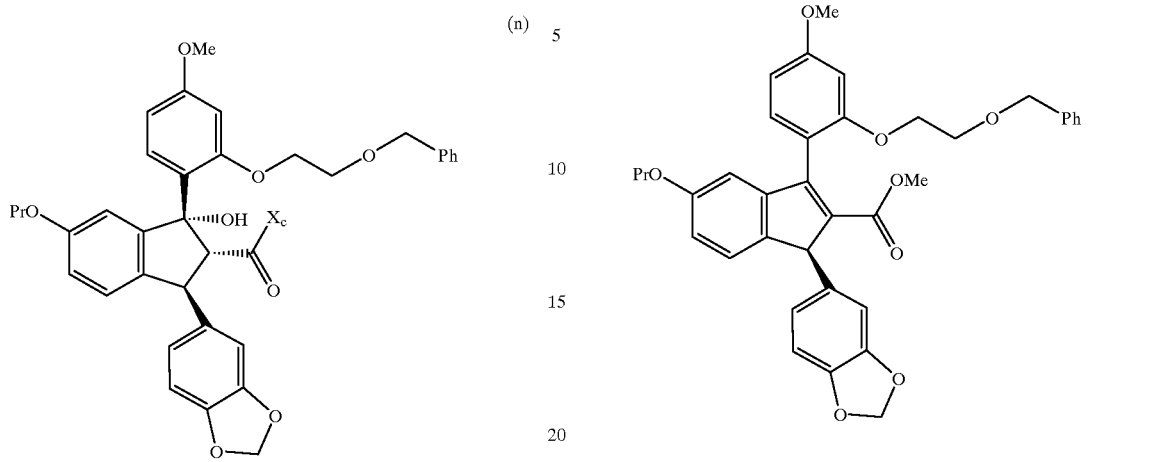

(n)

predominantly as the single enantiomer depicted, into a compound of formula (r), as described in claim 4, step (7), and thereafter optionally forming a pharmaceutically acceptable salt thereof.

17. A process for the preparation of a compound of formula (r), as described in claim 4, step (7), or a pharmaceutically acceptable salt thereof, which comprises converting a compound of the structure, (o)

predominantly as the single enantiomer depicted, into a compound of formula (r), as described in claim 4, step (7), and thereafter optionally forming a pharmaceutically acceptable salt thereof.

18. A process for the preparation of a compound of formula (r), as described in claim 4, step (7), or a pharmaceutically acceptable salt thereof, which comprises converting a compound of the structure, (p)

predominantly as the single enantiomer depicted, into a compound of formula (r), as described in claim 4, step (7), and thereafter optionally forming a pharmaceutically acceptable salt thereof.

19. A process for the preparation of a compound as described in claim 5, step (8), or a pharmaceutically acceptable salt thereof, which comprises converting a compound of the formula,

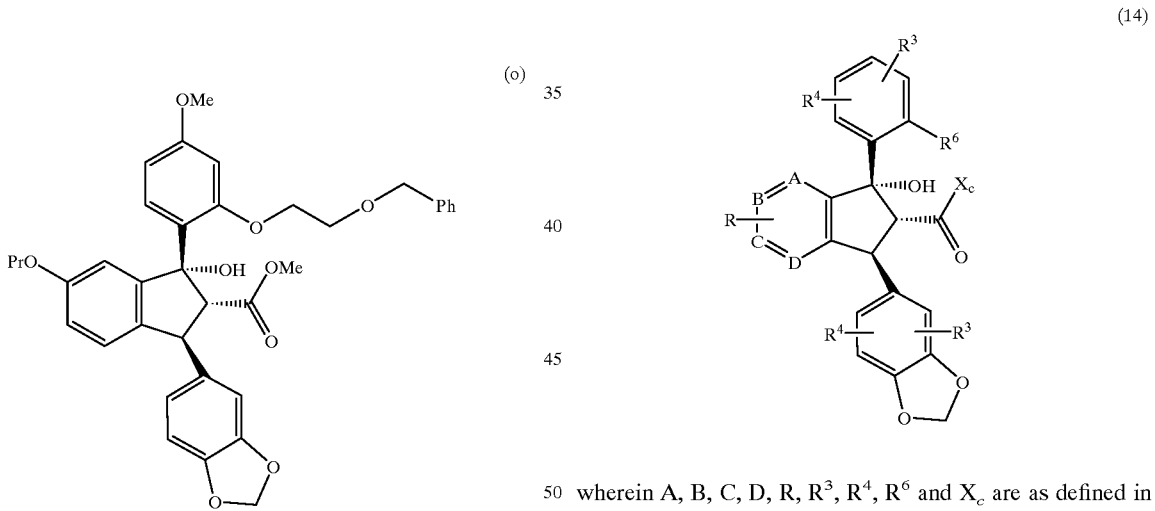

(14)

wherein A, B, C, D, R, $R^3$, $R^4$, $R^6$ and $X_c$ are as defined in claim 5, predominantly as the single enantiomer depicted into a compound as described in claim 5, step (8), and thereafter optionally forming a pharmaceutically acceptable salt thereof.

20. A process for the preparation of a compound as described in claim 5, step (8), or a pharmaceutically acceptable salt thereof, which comprises converting a compound of the formula, of the formula,

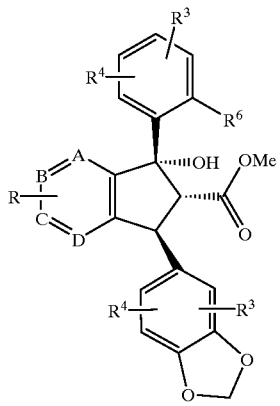

(15)

wherein A, B, C, D, R, R³, R⁴ and R⁶ are as defined in claim 5, predominantly as the single enantiomer depicted into a compound as described in claim 5, step (8), and thereafter optionally forming a pharmaceutically acceptable salt thereof.

21. A process for the preparation of a compound as described in claim 5, step (8), or a pharmaceutically acceptable salt thereof, which comprises converting a compound of the formula,

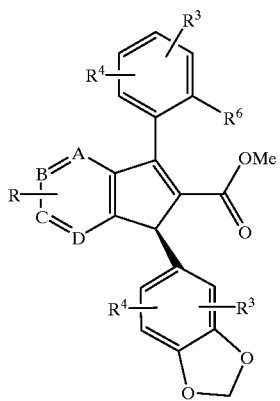

(16)

wherein A, B, C, D, R, R³, R⁴ and R⁶ are as defined in claim 5, predominantly as the single enantiomer depicted into a compound as described in claim 5, step (8), and thereafter optionally forming a pharmaceutically acceptable salt thereof.

22. A process for the preparation of a compound as described in claim 6, step (7), or a pharmaceutically acceptable salt thereof, which comprises converting a compound of the formula,

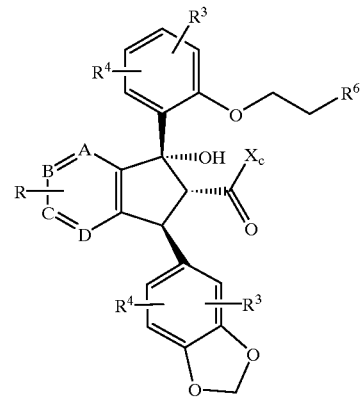

(23)

wherein A, B, C, D, R, R³, R⁴, R⁶ and $X_c$ are as defined in claim 6, predominantly as the single enantiomer depicted, into a compound as described in claim 6, step (7), and thereafter optionally forming a pharmaceutically acceptable salt thereof.

23. A process for the preparation of a compound as described in claim 6, step (7), or a pharmaceutically acceptable salt thereof, which comprises converting a compound of the formula,

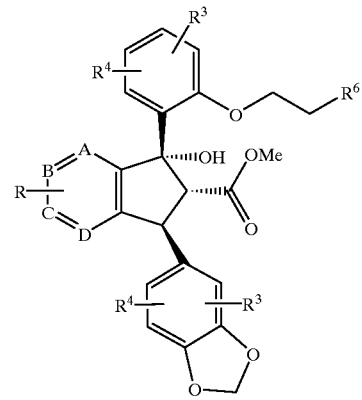

(24)

wherein A, B, C, D, R, R³, R⁴ and R⁶ are as defined in claim 6, predominantly as the single enantiomer depicted, into a compound as described in claim 6, step (7), and thereafter optionally forming a pharmaceutically acceptable salt thereof.

24. A process for the preparation of a compound as described in claim 6, step (7), or a pharmaceutically acceptable salt thereof, which comprises converting a compound of the formula, (25)

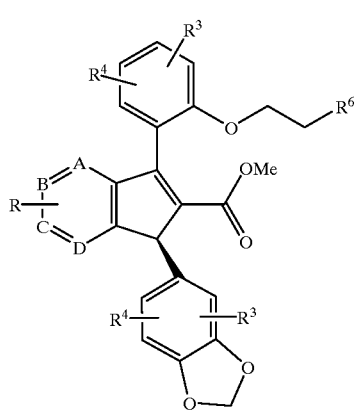

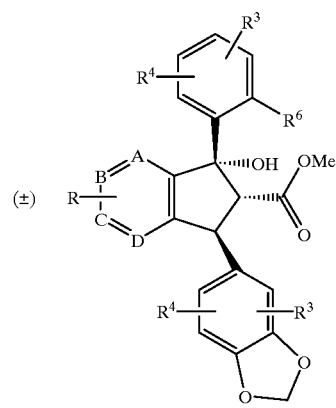

wherein A, B, C, D, R, R³, R⁴ and R⁶ are as defined in claim 6, predominantly as the single enantiomer depicted, into a compound as described in claim 6, step (7), and thereafter optionally forming a pharmaceutically acceptable salt thereof.

25. A process for the preparation of a compound as defined in claim 2, step (7), or a pharmaceutically acceptable salt thereof, which comprises converting a compound of the formula,

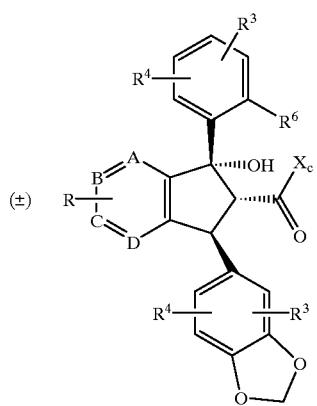

wherein A, B, C, D, R, R³, R⁴, R⁶ and $X_c$ are described in claim 2 into a compound as described in claim 2, step (7), and thereafter optionally forming a pharmaceutically acceptable salt thereof.

26. A process for the preparation of a compound as described in claim 2, step (7), or a pharmaceutically acceptable salt thereof, which comprises converting a compound of the formula, wherein A, B, C, D, R, R³, R⁴ and R⁶ are as defined in claim 2 into a compound as described in claim 2, step (7), and thereafter optionally forming a pharmaceutically acceptable salt thereof.

27. A process for the preparation of a compound as described in claim 2, step (7), or a pharmaceutically acceptable salt thereof, which comprises converting a compound of the formula,

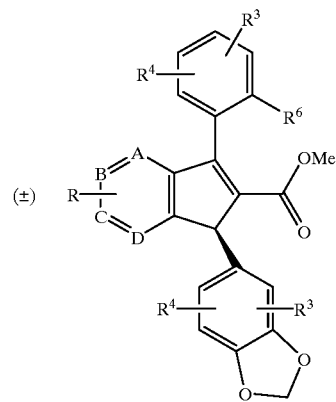

wherein A, B, C, D, R, R³, R⁴ and R⁶ are as defined in claim 2 into a compound as described in claim 2, step (7), and thereafter optionally forming a pharmaceutically acceptable salt thereof.

28. A process for the preparation of a compound of formula (r), as described in claim 4, step (7), or a pharmaceutically acceptable salt thereof, which comprises converting a compound of the structure,

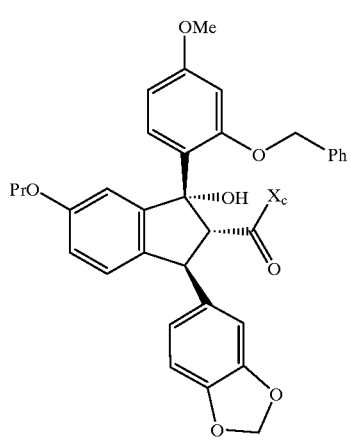
(f)

predominantly as the single diastereomer depicted, into a compound of formula (r), as described in claim 4, step (7), and therafter optionally forming a pharmaceutically acceptable salt thereof.

29. A process for the preperation of a compound of a formula (r), as described in claim 4, step (7), or a pharmaceutically acceptable salt thereof, which comprises converting a compound of the structure,

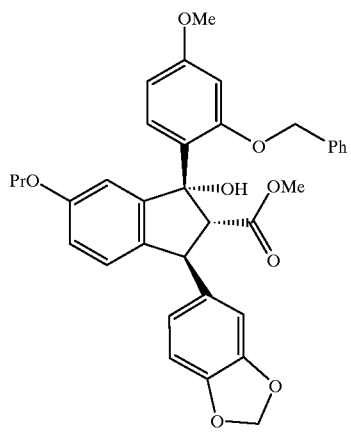
(g)

predominantly as the single enantiomer depicted, into a compound of formula (r), as described in claim 4, step (7), and thereafter optionally forming a pharmaceutically acceptable salt thereof.

30. A process for the preperation of a compound of formula (r), as described in claim 4, step (7), or a pharmaceutically acceptable salt thereof, which comprises converting a compound of the structure,

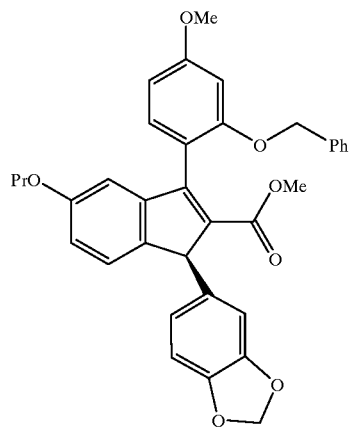
(h)

predominantly as the single enantiomer depicted, into a compound of formula (r), as described in claim 4, step (7), and thereafter optionally forming a pharmaceutically acceptable salt thereof.

31. A process for the preparation of a compound as described in claim 6, step (7), or a pharmaceutically acceptable salt thereof, which comprises converting a compound of the formula,

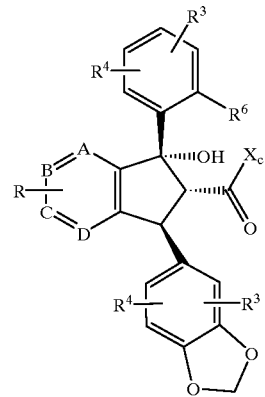
(14)

wherein A, B, C, D, R, $R^3$, $R^4$, $R^6$ and $X_c$ are as defined in claim 6, predominantly as the single enantiomer depicted, into a compound as described in claim 6, step (7), and thereafter optionally forming, a pharmaceutically acceptable salt thereof.

32. A process for the preparation of a compound as described in claim 6, step (7), or a pharmaceutically acceptable salt thereof, which comprises converting a compound of the formula,

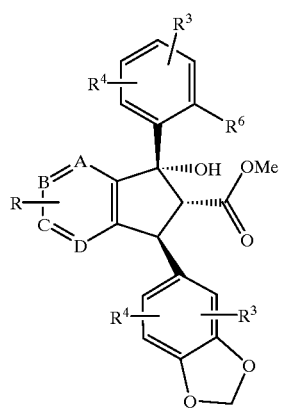

(15)

wherein A, B, C, D, R, $R^3$, $R^4$ and $R^6$ are as defined in claim 6, predominantly as the single enantiomer depicted, into a compound as described in claim 6, step (7), and thereafter optionally forming a pharmaceutically acceptable salt thereof.

33. A process for the preparation of a compound as described in claim 6, step (7), or a pharmaceutically acceptable salt thereof, which comprises converting a compound of the formula,

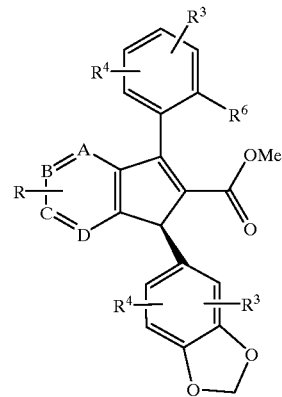

(16)

wherein A, B, C, D, R, $R^3$, $R^4$ and $R^6$ are as defined in claim 6, predominantly as the single enantiomer depicted, into a compound as described in claim 6, step (7), and thereafter optionally forming a pharmaceutically acceptable salt thereof.

* * * * *